United States Patent
Desai et al.

(10) Patent No.: US 12,127,883 B2
(45) Date of Patent: Oct. 29, 2024

(54) WETTING FOR USE IN PROLONGED IMAGING PROCEDURES

(71) Applicant: Cal Tenn Innovation, Inc., Jackson, TN (US)

(72) Inventors: Siddharth Desai, Mission Viejo, CA (US); Jerry Jones, Jackson, TN (US)

(73) Assignee: Cal Tenn Innovation, Inc., Jackson, TN (US)

(*) Notice: Subject to any disclaimer, the term of this patent is extended or adjusted under 35 U.S.C. 154(b) by 86 days.

(21) Appl. No.: 17/533,572

(22) Filed: Nov. 23, 2021

(65) Prior Publication Data
US 2022/0160330 A1 May 26, 2022

Related U.S. Application Data

(60) Provisional application No. 63/117,934, filed on Nov. 24, 2020.

(51) Int. Cl.
*A61B 8/00* (2006.01)

(52) U.S. Cl.
CPC .......... *A61B 8/4444* (2013.01); *A61B 8/4254* (2013.01); *A61B 8/46* (2013.01)

(58) Field of Classification Search
CPC ....... A61B 8/4444; A61B 8/4254; A61B 8/46; A61B 8/0866; A61B 8/4455; A61B 8/4281; A61B 8/4422
See application file for complete search history.

(56) References Cited

U.S. PATENT DOCUMENTS

| | | | | |
|---|---|---|---|---|
| 4,787,070 | A * | 11/1988 | Suzuki | A61B 8/4281 601/2 |
| 5,494,038 | A * | 2/1996 | Wang | G01N 29/28 73/644 |
| 10,206,653 | B2 * | 2/2019 | Desai | A61B 8/4281 |
| 10,980,510 | B2 * | 4/2021 | Scully | A61B 8/4422 |
| 11,600,201 | B1 * | 3/2023 | Savitsky | A61B 8/4455 |
| 2002/0068871 | A1 * | 6/2002 | Mendlein | A61B 8/4209 600/459 |

(Continued)

FOREIGN PATENT DOCUMENTS

| CN | 206120352 U | 4/2016 |
|---|---|---|
| CN | 206729907 U | 12/2017 |

(Continued)

OTHER PUBLICATIONS

Search Report for International Patent Application PCT/US2021/060516, mailed on Mar. 24, 2022, 7 pages.

*Primary Examiner* — Adil Partap S Virk
(74) *Attorney, Agent, or Firm* — Fresh IP PLC; John R. Bednarz

(57) ABSTRACT

Described herein are accelerator devices for providing a couplant while moving an ultrasound probe over a surface. The devices may include a reservoir configured to hold ultrasound couplant. The reservoir may attach to a probe so as to dispense the couplant at one or more locations along a perimeter of the probe while moving the ultrasound probe over the surface. The devices may additionally, or alternatively, include a membrane configured to hold ultrasound couplant. The membrane may charge a couplant layer of an ultrashield prior to or while moving the ultrasound probe over a surface during an ultrasound procedure.

9 Claims, 21 Drawing Sheets

(56) References Cited

U.S. PATENT DOCUMENTS

| | | | | |
|---|---|---|---|---|
| 2006/0241423 A1* | 10/2006 | Anderson | ............ | A61B 8/5238 |
| | | | | 600/437 |
| 2007/0038097 A1* | 2/2007 | Crawford | ................. | A61B 8/12 |
| | | | | 600/439 |
| 2012/0209114 A1* | 8/2012 | Staalsen | ............... | A61B 8/4455 |
| | | | | 600/407 |
| 2013/0211250 A1* | 8/2013 | Brocardo | ................. | A61N 7/02 |
| | | | | 523/105 |
| 2015/0231415 A1* | 8/2015 | Lewis, Jr. | ............. | A61B 8/4236 |
| | | | | 601/2 |
| 2016/0051228 A1* | 2/2016 | Nakai | ................. | A61B 8/4444 |
| | | | | 600/407 |
| 2020/0108178 A1* | 4/2020 | Engel Lopez | ......... | A61K 31/08 |
| 2020/0383660 A1* | 12/2020 | Rothberg | ............. | A61B 8/4281 |

FOREIGN PATENT DOCUMENTS

| | | | |
|---|---|---|---|
| CN | 108836452 A | 11/2018 | |
| WO | 2019147940 A1 | 8/2019 | |

\* cited by examiner

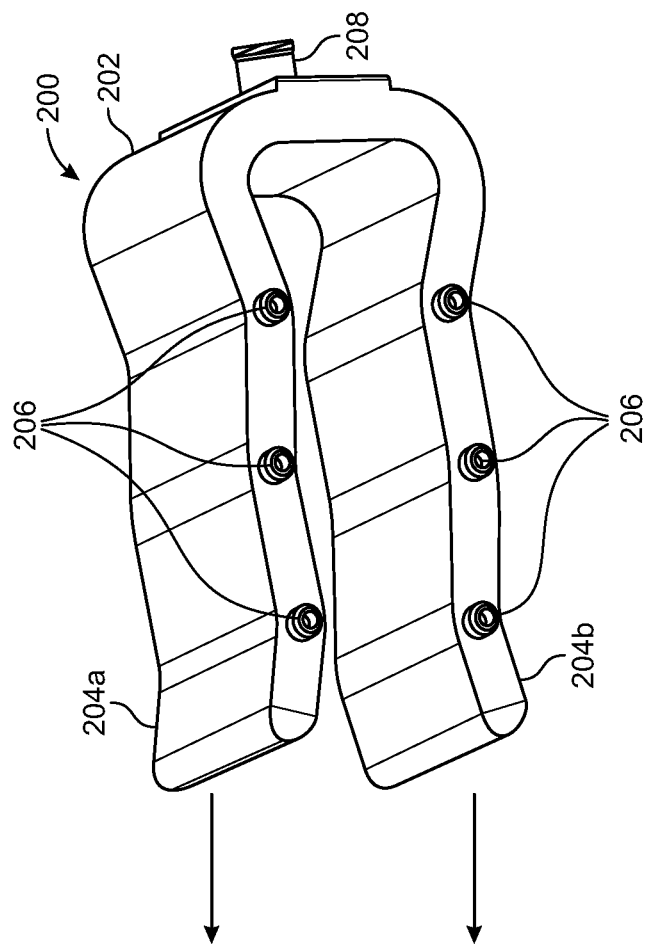
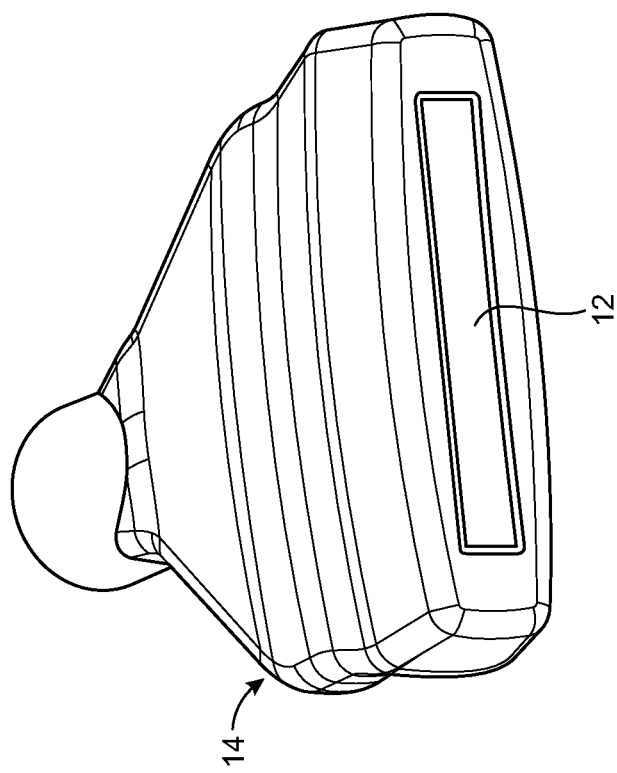
FIG. 23B
FIG. 23A

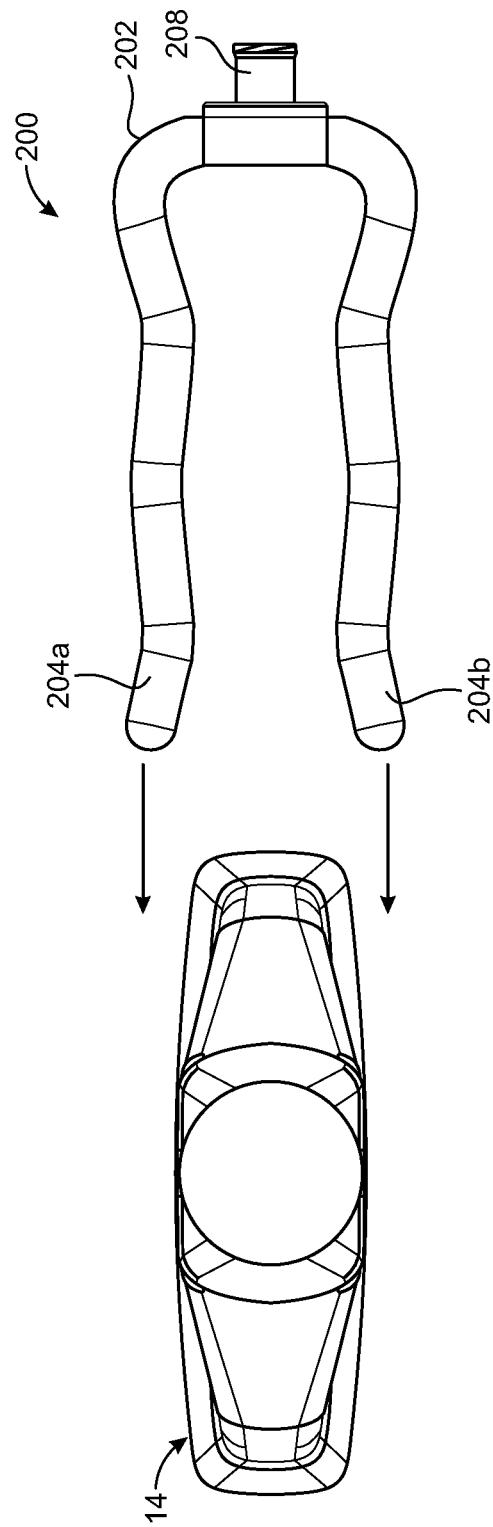

WETTING FOR USE IN PROLONGED IMAGING PROCEDURES

CROSS-REFERENCE TO RELATED APPLICATION

This application is related to and claims priority under 35 U.S.C. § 119(e) to U.S. Patent Application No. 63/117,934, filed Nov. 24, 2020, entitled "Improved Wetting for Use in Prolonged Imaging Procedures," the disclosure of which is hereby incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

The application of ultrasound in medicine began in the 1950s. It was first introduced in the field of obstetrics. Obstetric sonography is the use of medical ultrasonography in pregnancy, in which sound waves are used to create real-time visual images of the developing embryo or fetus in its mother's uterus. The procedure is a standard part of prenatal care in many countries, as it can provide a great deal of information about the health of the mother, the timing and progress of the pregnancy, and the health and development of the embryo or fetus. After that, the use of ultrasound propagated to nearly all fields of medicine including abdominal diagnostics, cardiology, urology, cerebrovascular, ophthalmology, orthopedics, breast examination, and pediatrics. Ultrasound has been proven to provide fast, accurate and safe patient imaging for an expanding array of diagnostic and therapeutic applications with ongoing technologic improvements and the growing recognition of harmful radiation from other imaging modalities.

Sonographers typically use a hand-held probe (called a transducer) that is placed directly on and moved over the patient. With the use of the probe, the sonographer is able to visualize body structures under the skin including tendons, muscles, joints, nerves, vessels and internal organs for possible pathology or lesions. Current probes utilize reflection technology. The probe transmits high-frequency ultrasound sound pulses into the body. The pulses are produced by a piezoelectric transducer within the probe. Strong, short electrical pulses from the ultrasound machine cause the crystals to change shape rapidly. The rapid shape changes, or vibrations, of the crystals produce sound waves that travel outward. The ultrasound wave travels into the body until it encounters a boundary between tissues (e.g. between fluid and soft tissue, soft tissue and bone). Some of the ultrasound waves get reflected back to the probe, while some travel on further until they reach another boundary and get reflected. The reflected waves are picked up and interpreted by the probe to produce a real-time two-dimensional representation on a monitor. Interpretation through the probe occurs when the reflected sound or pressure waves hit the piezoelectric crystals which causes them to emit electrical currents. Thus, the same crystals can be used to send and receive sound waves. The probe also has a sound absorbing substance to eliminate back reflections from the probe itself. The electric currents generated by the reflected waves are relayed to the ultrasound machine. The ultrasound machine is able to calculate the distance from the probe to the tissue or organ (boundaries) using the speed of sound in tissue (5,005 ft/s or 1,540 m/s) and the time of each echo's return (usually on the order of millionths of a second). The ultrasound machine then displays the distances and intensities of the echoes on the screen, forming a two dimensional image. 3D images can be generated by acquiring a series of adjacent 2D images by simply moving or tilting the probe on the patient.

In order for the maximal transmission of energy from one medium to another (i.e., from the probe through the skin), the impedance of the two media should be nearly the same. Clearly, in the case of ultrasound waves passing from the probe to the tissues, this cannot be readily achieved. The greater the difference in impedance at a boundary, the greater the reflection that will occur, and therefore, the smaller the amount of energy that will be transferred. With decreased sound waves transferred, there is less energy to be reflected and interpreted by the probe. The difference in impedance is greatest for the probe/air interface which is the first one that the ultrasound has to overcome in order to reach the body. Therefore, maintaining constant and optimal contact between the probe and skin is important for the utilization of ultrasound technology. This is typically achieved with the use of a suitable coupling medium. Conventional coupling media include various oils, creams and gels. These fluids and gels commonly used as ultrasound couplants have several fundamental disadvantages, some of which are described herein. To begin, patients often find the fluid or gel to be cold, sticky and messy. The fluids or gels are difficult to contain on, and remove from, the patient during and after the ultrasound procedure. Further, commercially available oils and water based gels often introduce problems to the electronics by their chemically degrading nature. They may react with the adhesives, elastomers, and epoxies used in the construction of medical ultrasound transducers, thus appreciably degrading performance and shortening their service life.

In addition, fluids and gels offer no microbial barrier between the patient and the probe transducer; thus, latex rubber or synthetic elastomer probe covers must be applied over the probe transducer, to prevent transmission of microorganisms to the patient. Often, two layers of couplant, one inside and one outside the probe cover, are required to provide ultrasound acoustic coupling between the transducer and the patient. This potential infection concern is readily apparent when the transducer is used for imaging during needle biopsy or aspiration, or inside the body during surgery in direct organ, tissue and blood contact. Of growing importance is the protection from infection by skin transmission to patients who are immune compromised by disease, organ replacement, immune system modification, chemotherapy, or radiation treatments.

Although alternatives to these conventional couplants have been developed, some challenges have remained in some instances, particularly in prolonged imaging procedures. Typically, there are three stages in the process of imaging: 1) static imaging, 2) dynamic imaging and 3) prolonged imaging. At the start of a procedure, a couplant must be available to allow immediate imaging in a static configuration. This is considered static imaging when the probe is not moving. The couplant should be uniform across the tissue to provide a consistently uniform image. Any absence or unevenness typically inhibits the image and provides inadequate quality. Dynamic imaging begins with movement of the probe. During dynamic movement, the couplant should be able to provide a continuous image. Many procedures are of short duration. For smaller tissue diagnostics, such as a nerve block, the duration may be less than 9 minutes. However, other procedures may be of longer duration. For example, typical imaging process times are an average of 30 minutes for a pregnancy test and may last longer. Prolonged imaging may occur for procedures lasting longer than 30 minutes. It is often during these procedures that couplant availability becomes increasingly challenging and arduous.

Therefore, improved methods and devices are desired to reliably and safely provide maximal transmission of acoustic energy during ultrasound imaging while reducing fundamental disadvantages associated with the conventional use of ultrasound couplants. In particular, such improved methods and devices will provide such maximal transmission through each stage in the process of imaging. At least some of these objectives will be met by the present disclosure.

SUMMARY

According to one aspect, an accelerator device for providing couplant while moving an ultrasound probe over a surface includes a reservoir configured to hold ultrasound couplant, wherein the reservoir is configured to attach to a probe so as to dispense the couplant at one or more locations along a perimeter of the probe while moving the ultrasound probe over the surface.

According to another aspect, an accelerator membrane for providing couplant includes a membrane configured to hold ultrasound couplant, wherein the membrane is configured to charge a couplant layer of an ultrashield prior to or while moving the ultrasound probe over a surface during an ultrasound procedure.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 23A-23B illustrate an embodiment of a probe and an accelerator device that is positionable at least partially around the probe to deliver couplant and/or other materials to the surface upon which the probe is placed according to an example of the instant disclosure.

FIGS. 24A-24B provide a top view of the probe and accelerator device of FIGS. 23A-23B according to an example of the instant disclosure.

DETAILED DESCRIPTION

Specific embodiments of the disclosed devices and methods will now be described with reference to the drawings.

In some embodiments, the methods, systems and devices described herein are improvements upon an ultrashield or systems including an ultrashield. Example embodiments of ultrashields and systems including an ultrashield are provided in U.S. Pat. No. 10,206,653 entitled, "ULTRASHIELD DEVICES AND METHODS FOR USE IN ULTRASONIC PROCEDURES", U.S. Pat. No. 10,064,599 entitled, "ULTRASHIELD DEVICES AND METHODS FOR USE IN ULTRASONIC PROCEDURES", and U.S. patent application Ser. No. 16/249,724, entitled "ULTRASHIELD DEVICES AND METHODS FOR USE IN ULTRASONIC PROCEDURES", all of which are incorporated herein by reference for all purposes.

Figure 1:
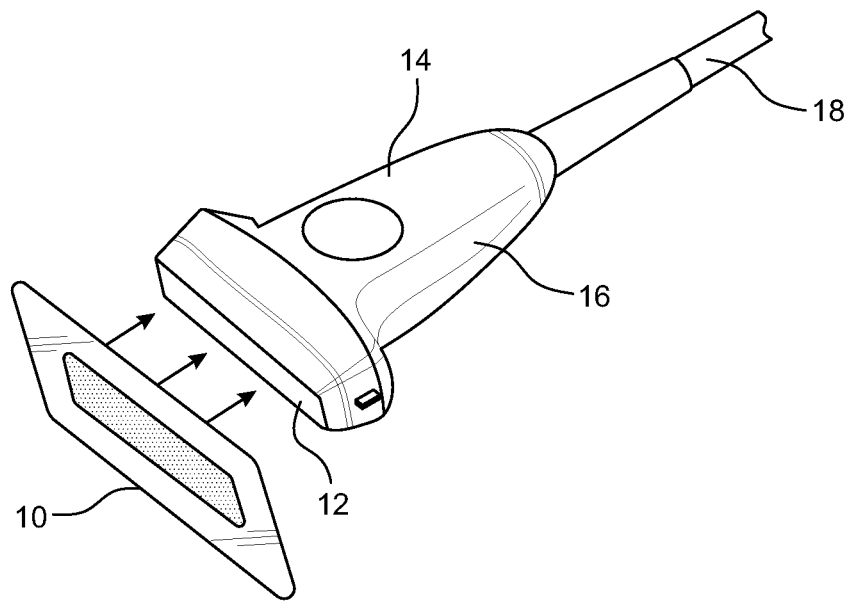
FIG. 1 illustrates an embodiment of an ultrashield and a probe to which the ultrashield is affixable according to an example of the instant disclosure.
Figure 2:
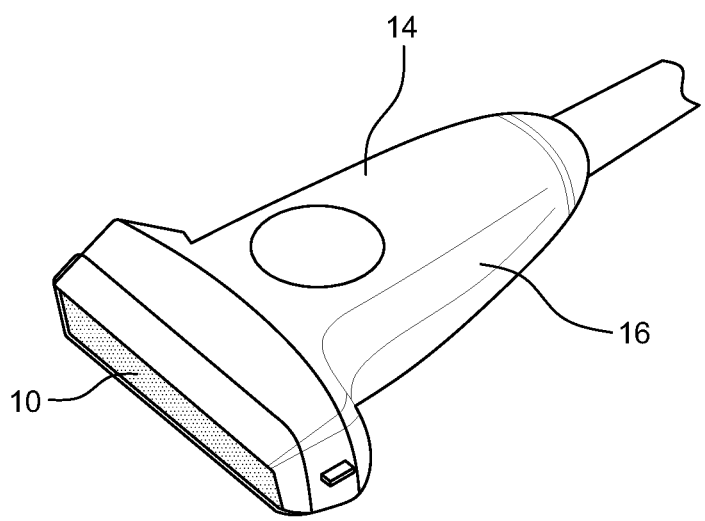
FIG. 2 illustrates an ultrashield sized and configured so that portions of its exterior edge wrap around the probe according to an example of the instant disclosure.

An ultrashield is typically used with a conventional ultrasound probe and eliminates the need for additional ultrasonic couplants, such as gels. In some embodiments, the ultrashield is a cover or shield which is positioned over the faceplate of an ultrasound probe, either alone or in conjunction with a probe cover. FIG. 1 illustrates an embodiment of an ultrashield 10 which is sized and configured to affix to the faceplate 12 of an ultrasound probe 14, as indicated by arrows. Typically, the ultrashield 10 is sized and configured so that portions of its exterior edge wrap around the probe 14, beyond the faceplate 12, so as to ensure a complete seal, as illustrated in FIG. 2. The ultrasound probe 14 comprises a housing 16 which contains the piezoelectric crystal, electrodes, and acoustic insulator. The housing 16 is connected with a coaxial cable 18 which extends to the ultrasound machine (not shown). The ultrasound waves are transmitted from the piezoelectric crystal through the faceplate 12, to the body of the patient. By affixing the ultrashield 10 to the faceplate 12, the ultrasound waves pass directly through the ultrashield 10, without introducing an air barrier or a significant difference in impedance. Likewise, when the probe 14 is in use, the ultrashield 10 contacts the surface of the patient, again without introducing a barrier or a significant difference in impedance. Particular features of the ultrashield 10 allow its use without a traditional external gel couplant.

Figure 3A:
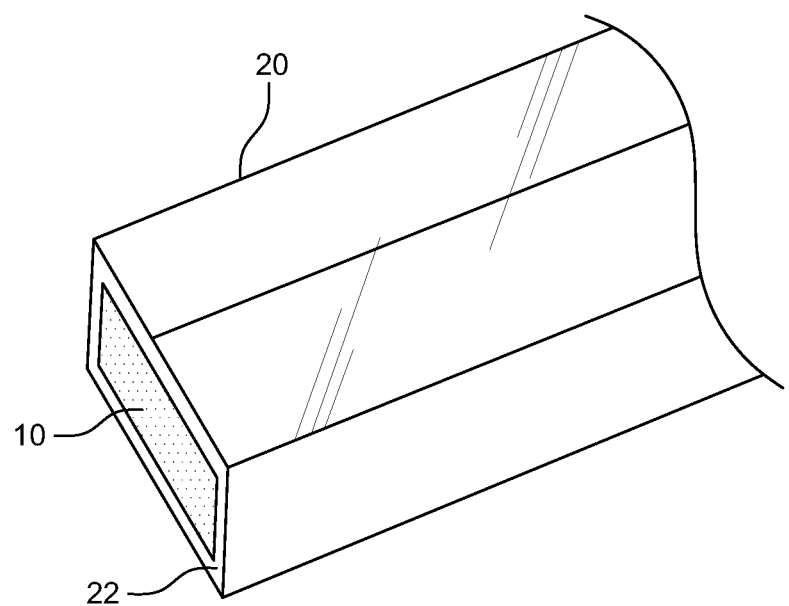
FIGS. 3A-3B illustrate an embodiment of a probe cover having an ultrashield according to an example of the instant disclosure.
Figure 3B:
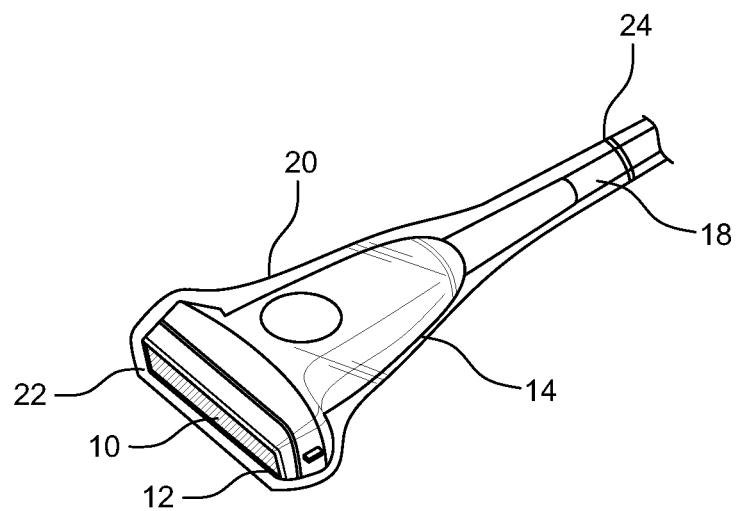

FIGS. 3A-3B illustrate an embodiment of a probe cover 20 having an ultrashield 10. Such a probe cover 20 is typically used in sterile conditions in an operating room. The probe cover 20 allows the use of the probe 14 in scanning and needle guided procedures for body surface, endocavity and intra-operative diagnostic ultrasound procedures, while helping to prevent transfer of microorganisms, body fluids and particulate material to the patient and healthcare worker during reuse of the probe 14. The probe cover 20 provides an extremely important need which is to provide a removable barrier between the probe 14 and the individual patient which will prevent infectious particles from being transmitted to different patients due to inadequate cleanings of the probe between uses. Such a barrier between the patient and the probe 14 (that is exchanged between probe uses) is particularly important for many probes 14 which have crevices and contours that have been found to be very difficult to definitively clean, leading to an increased risk of spreading infectious particles.

In this embodiment, the probe cover 20 has an oblong, rectangular shape, as illustrated in FIG. 3A, with a bottom surface 22 having a rectangular shape for use with a probe having a rectangular shaped faceplate 12. However, it may be appreciated that such probe covers 20 may have various shapes and forms for accommodating various types of probes. In this embodiment, the ultrashield 10 is disposed along the bottom surface 22. The cover 20 is then positioned over the probe 20. FIG. 3B illustrates the probe cover 20 of FIG. 3A positioned on a probe 14. Here, the ultrashield 10 is aligned with the faceplate 12 of the probe 14 and the cover 20 is pulled up tightly around the probe, so as to remove any wrinkles, taking care to avoid puncturing the cover. The cover 20 may be secured to the cable 18 with bands 24. In some embodiments, the probe cover 20 includes adhesive along a portion of its inner walls or surfaces to hold the cover 20 snugly to the probe 14. In some embodiments, the probe cover 20 also includes an adhesive disposed along the inside of the probe cover 20 at a location so as to adhere the probe cover 20 directly to the faceplate 12 of the probe 14. It may be appreciated that the adhesive may cover a variety of surfaces of the probe cover 20 to assist in adhering the ultrashield 10 to the probe 14. It may be appreciated that in some embodiments the ultrashield 10 is separate from the probe cover 20 and can be adhered to a surface of the probe cover 20 for use. Thus, rather than adhering the probe contact layer 30 directly to the probe 14, the probe contact layer 30 is adhered to the probe cover 20. This allows the user to utilize the ultrashield 10 with any probe cover 20 or similar device.

The use of such a specialized probe cover 20 eliminates the need for application of a gel couplant inside the cover and/or on the faceplate. This saves preparation time, reduces damage to the probe, eliminates the possibility of puncture and leakage of gel, reduces clean up time and eliminates the possibility of cross-contamination due to gel residue trapped in the probe 14.

As mentioned, when the clinician starts ultrasonic imaging, the probe 14 is able to visualize through the ultrashield 10 and it moves along with the probe 14. The separate gel couplant is not required due to the specialized properties of the ultrashield 10 that provide ultrasonic conductivity along with ease of gliding over the patient skin or body surface. Such specialized properties are provided by various layers that make up the ultrashield 10. These layers are also echogenic and facilitate transmission of ultrasonic waves with minimal or no loss.

Figure 4:
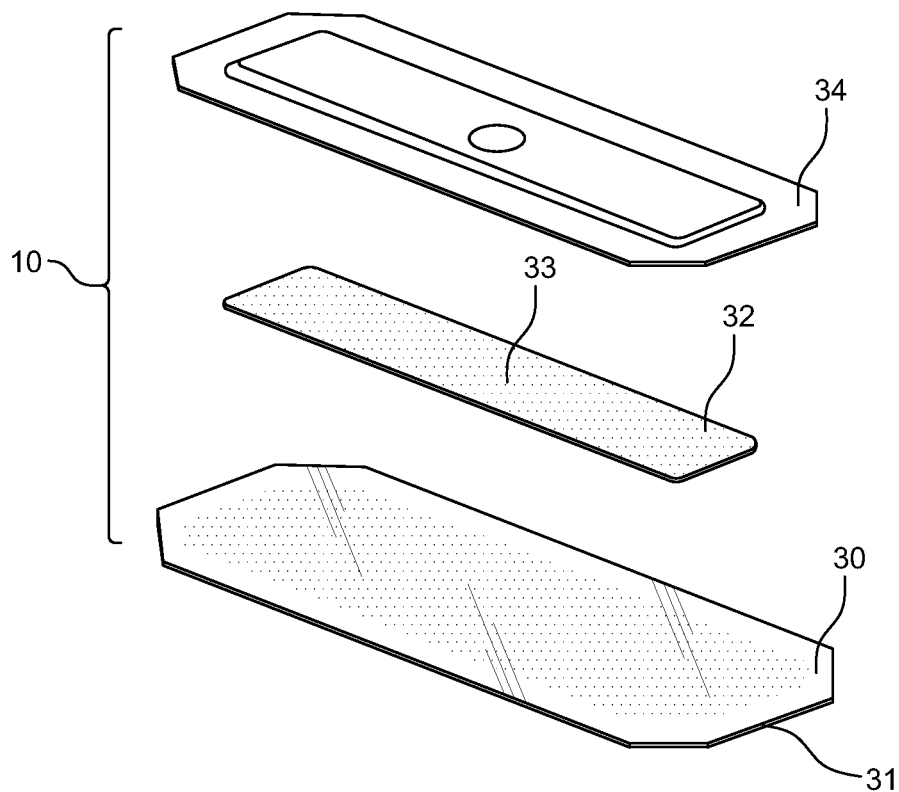
FIG. 4 illustrates an embodiment of an ultrashield in an expanded view according to an example of the instant disclosure.

FIG. 4 illustrates an embodiment of an ultrashield 10 in an expanded view revealing various layers. In this embodiment, the layers include a probe contact layer 30, an intermediate sandwich layer or couplant layer 32, and an outer surface body contact layer 34. These layers will be described in more detail below.

Figure 5:
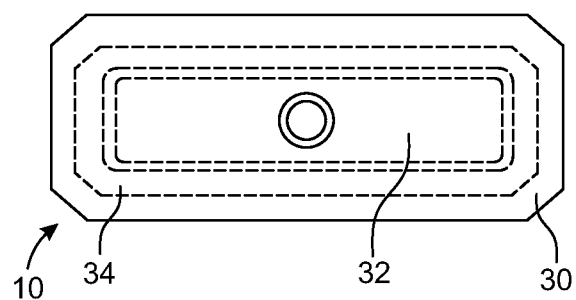
FIG. 5 illustrates the ultrashield embodiment of FIG. 4 in an unexpanded view according to an example of the instant disclosure.

FIG. 5 illustrates the ultrashield 10 embodiment of FIG. 4 in an unexpanded view wherein the layers 30, 32, 34 are stacked and adhered together to form a single multi-layered sheet. As shown, the ultrashield 10 has a thin, compact design which is easily packaged, handled, and applied to the head of a probe 14. It may be appreciated that the ultrashield 10 may take a variety of forms. In some embodiments, the ultrashield 10 includes all of the layers depicted in FIGS. 4-5, however the ultrashield may have more layers or less layers. For example, in some embodiments, aspects of a particular layer are provided by another layer of the ultrashield 10 or the probe cover 20.

Probe Contact Layer

The probe contact layer 30 provides an integrated polymeric surface that connects with the probe 14 and gives a connection that is substantially free of any air or vacuum. This ensures that the ultrashield 10 will be integral to the probe 14 as a 'seamless' surface. The probe contact layer 30 is typically comprised of a flexible film, such as flexible polymer film. In some embodiments, the film includes a rigid layer, such as a rigid center layer, to provide additional structure. The central rigid layer typically resides along the portion of the probe contact layer 30 that covers the faceplate 12 of the probe 14, allowing a more flexible portion of the contact layer 30 (such as disposed around the rigid center layer) to bend around the probe 14.

In some embodiments, the contact layer 30 has a thickness in the range of 0.010 to 0.060 inches, more particularly 0.030 to 0.060 inches. Similarly, in some embodiments, the contact layer 30 has a thickness of less than or equal to 0.060 inches, less than or equal to 0.050 inches, less than or equal to 0.040 inches, or less than or equal to 0.020 inches. In some embodiments, the contact layer 30 is comprised of quartz or a polymer such as polyethylene, polyurethane, polypropylene, polyester, ethylene vinyl acetate, polyvinyl chloride, or the like. In each of these instances, the layer 30 has a low level of attenuation co-efficient and shall provide minimal or no diminishment of ultrasound wave transmission.

Typically, the probe contact layer 30 includes an adhesive 31 on at least one side of the contact layer 30. The adhesive 31 allows the ultrashield 10 to be affixed to the probe 14, such as the faceplate 12 of the probe 14 and optionally the housing 16. This creates an airless connection between the ultrashield 10 and the probe 14. In some embodiments, the probe contact layer 30 includes an adhesive 31 to adhere the couplant layer 32 and/or the outer surface body contact layer 34 thereto. In other embodiments, the ultrashield 10 is attachable to or integral with a probe cover. In yet other embodiments, the ultrashield 10 is attachable to or integral with a retainer module which is easily attachable to the probe 14. The retainer module will be described in more detail in later sections. Both the probe cover and the retainer module avoid direct attachment of the ultrashield 10 to the faceplate 12, such as with adhesive.

Typically, the adhesive 31 has a very fine thickness, such as 0.001 to 0.005 inches, more particularly 0.002 to 0.003 inches. Example adhesives 31 include epoxy, polyurethane, cyanoacrylate and acrylic polymers, to name a few. In some embodiments, the adhesive 31 comprises a pressure adhesive wherein upon application of pressure the contact layer 30 adheres to the probe 14 and when it is pulled for removal it leaves behind negligible or no residue. It may be appreciated that the adhesive 31 shall provide minimal or no diminishment of ultrasound wave transmission as well.

Couplant Layer

In this embodiment, the couplant layer 32 comprises a couplant material 33 such as a hydrogel, collagen material, polymer matrix and/or thermoplastic elastomer containing a couplant. The couplant material 33 has a very low acoustic attenuation coefficient, such as 0.05 dB/cm/MHz or less at a frequency of 1540 MHz (human tissue), so that it transmits the ultrasonic wave with minimal to no loss of energy. The lower the attenuation coefficient, the better is the transmission of ultrasonic wave through the material. In preferred embodiments, the couplant within the couplant material 33 comprises water which has the lowest attenuation coefficient. However, other couplants may be used such as glycerin, silicone oil, silicone gel, or other ultrasound gels, that have very low attenuation coefficients. The couplant layer 32 typically has a thickness in the range of approximately 0.060 to 0.150 inches, more particularly 0.010 to 0.040 inches. Likewise, the couplant layer 32 is typically flexible or pliable by means of a low durometer profile, such as a durometer between 10-20 Shore A-2.

In some embodiments, the couplant material 33 is comprised of a hydrogel material that retains water in a colloidal condition for extended periods of time. Hydrogels are polymer networks extensively swollen with water. Hydrogels are made of crosslinked water-soluble polymers. Because of the crosslinks, hydrogels can absorb water and get swollen, but cannot be dissolved. In particular, the ability of hydrogels to absorb water arises from hydrophilic functional groups attached to the polymeric backbone, while their resistance to dissolution arises from cross-links between network chains. Through many intricate customizations, a hydrogel can be sensitive or responsive to the fluctuations in its external environment, such as temperature, pH, ionic strength, electric stimulus, etc. Hydrogels inherently possess a degree of flexibility very similar to natural tissue due to their large water content. Such flexibility, along with the ability to be formed into sheets and the ability to retain water, make hydrogels a desired couplant layer.

In some instances, the couplant layer 32 is inherently adhesive. For example, couplant materials 33 having greater than 95% water are typically self-adhesive. In such instances, the couplant layer 32 may adhere to the probe contact layer 30 and/or outer surface body contact layer 34 without additional adhesives 31.

Figure 6:
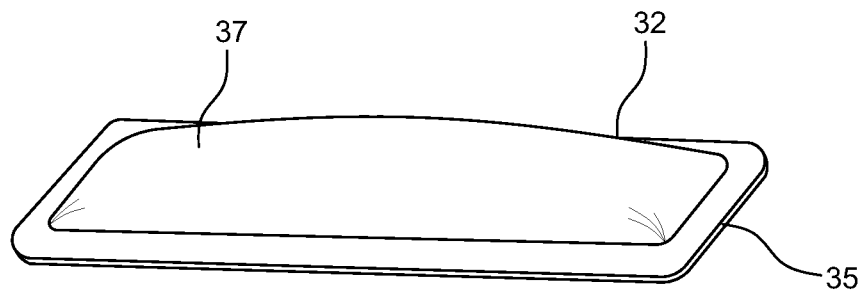
FIG. 6 illustrates an embodiment of a couplant layer comprising a couplant pouch according to an example of the instant disclosure.

In other embodiments, the couplant layer 32 comprises a couplant pouch 35 containing a couplant 37, as illustrated in FIG. 6. In such embodiments, the couplant pouch 35 has similar dimensions or volume as a couplant material 33 with a thickness of approximately 0.030 inches (30 mil) for fill volume. The probe contact layer 30 is typically comprised of a flexible polymer such as polyethylene, polyurethane, polypropylene, polyester, ethylene vinyl acetate, polyvinyl chloride, or the like. In each of these instances, the couplant pouch 35 has a low level of attenuation co-efficient and shall provide minimal or no diminishment of ultrasound wave transmission.

The couplant pouch 35 is filled with one or more couplants 37 and/or other materials, such as preservatives or additives. For example, in some embodiments the couplant pouch 35 is filled with one or more of the following:

Water (such as 7732-18-5)
Silicone oil
Silicone gel
Propylene Glycol (such as 57-55-6)
Ultrasound gel
Glycerin (such as 56-81-5)
Corrosion Inhibitors
Carboxy Polymethylene (such as 9003-01-4)

Cellulose (such as 9004-62-0)
Amino Alcohol
Surfactant
Preservative (such as 78491-02-8)

It may be appreciated that in some embodiments, the couplant layer 32 is comprised of conventional ultrasound gel or lotion. Thus, in some embodiments, the couplant layer 32 is comprised of a thin layer of conventional ultrasound gel itself. Alternatively, in other embodiments, the couplant layer 32 is comprised of a couplant material 33 which includes conventional ultrasound gel or lotion, or the couplant layer 32 is comprised of a couplant pouch 35 which includes conventional ultrasound gel or lotion.

In each of the embodiments described herein, the couplant layer 32 is selected for its favorable ultrasonic wave transmission ability. Since the layer 32 does not come in direct contact with the tissue or skin of the patient, the choice of couplant layer 32, material 33, or pouch 35 is not limited by other parameters, such as wearability, coefficient of friction, or adhesion. Therefore, the couplant layer 32, couplant material 33, or couplant pouch 35 providing superior ultrasonic transmission ability may be used. Likewise, in each of these embodiments, the couplant layer 32 forms an air pocket-free layer to provide superior ultrasonic without the need for additional external couplants such as conventional gels.

Outer Surface Body Contact Layer

The outer surface body contact layer 34 is configured to glide easily over the tissue or skin of the patient's body against which it is in contact. Thus, the body contact layer 34 is the outermost surface of the probe 14 when the ultrashield 10 is mounted thereon. Such glide-ability is due to various characteristics of the body contact layer 34. To begin, in some embodiments, the body contact layer 34 is comprised of a material having a low coefficient of friction. The coefficient of friction is the ratio between the force of sliding friction and the normal force. In some embodiments, the body contact layer 34 has a coefficient of friction that is less than or equal to the coefficient of friction of natural human skin, such as dry skin unwetted by emollients, lotions, or petrolatums. The coefficient of friction for natural skin varies across the human body. The palm of the hand has the highest coefficient of friction on the body, in the range of approximately 0.4-0.84 (0.62+/−0.22). However, the average coefficient of friction for natural skin is in the range of approximately 0.31-0.61 (0.46+/−0.15). Thus, in some embodiments, the body contact layer 34 has a coefficient of friction that is less than or equal to the coefficient of friction of the palm of the hand (less than 0.84, less than 0.62, or less than 0.4, to name a few). Likewise, in some embodiments, the body contact layer 34 has a coefficient of friction that is less than the average coefficient of friction of natural skin (less than 0.61, less than 0.046, or less than 0.31, to name a few). Thus, in some embodiments, the body contact layer 34 has a coefficient of friction of less than or equal to 0.5. In preferred embodiments, the body contact layer 34 has a coefficient of friction that is less than or equal to 0.1.

This is in contrast to a typical hydrogel which alone typically has a coefficient of friction that is greater than 1. In some embodiments, the body contact layer 34 is comprised of a film having a low coefficient of friction, such as polyester, polyvinylidene fluoride (PVDF), and polytetrafluoroethylene (PTFE) or TEFLON™. It may be appreciated that in some embodiments, the contact layer 36 is plasma treated or coated with a fine film of biocompatible material to reduce friction. In some embodiments, the body contact layer 34 has a thickness in the range of approximately 0.010 to 0.070 inches, more particularly 0.020 to 0.060 inches.

The outer surface body contact layer 34 has controlled openings, such as submicron or micron sized openings (e.g., 1 nm, 0.05 μm to 2.0 μm), which both assist in retention of couplant within the adjacent couplant layer 32 and allow a slow release of the couplant from the couplant layer 32 to the skin or body surface. Thus, the body contact layer 34 can be considered as a filter itself or it may be comprised of such a filter. In such embodiments, the body contact layer 34 may comprise openings of uniform or varying sizes, including 0.2-2.0 micron, 0.5-5 micron, 1 micron, 2 micron, 3 micron, 4 micron, 5, micron, up to 10 micron, and 10 micron, to name a few. The release of couplant creates an uninterrupted pathway of acoustic conductance from the probe 14 to the skin or body surface of the patient. In other words, the release of couplant to the body surface causes the body surface to be acoustically conductive with the ultrasound. In many instances, the couplant is water which is non-obtrusive to the patient and easily absorbed, evaporated, or wiped away after the procedure. Likewise, the body contact layer 34 is typically hydrophilic so as to be acoustically conductive as well.

In some embodiments, the body contact layer 34 creates a stretchable surface that moves axially as the probe 14 is moved over the tissue or skin of the patient so as to mimic the conventional gel function without compromising the body contact layer 34 and the body interface. In some embodiments, the body contact layer 36 is comprised of a membrane with at least 50% elongation to allow the probe 14 to adhere to the skin of body surface.

In some embodiments, the body contact layer 34 is sufficiently flexible so as to allow the compression of the sandwich layer 32. It may be appreciated that many liquids, such as water, are essentially incompressible. Therefore, when the sandwich layer 32 includes one or more liquids, the contact layer 34 is expandable to allow for shifting of the liquid due to compression of the sandwich layer 32 by the probe 14.

In some embodiments, the body contact layer 34 creates a breathing surface so that any potential air trapped between the skin and the body contact layer 34 is moved away from the body contact layer 34. In some instances, couplant, such as water, exiting the body contact layer 34 pushes any trapped air outward, creating a continuous ultrasonic connection.

It may be appreciated that it is desired that the ultrashield provide sufficient or abundant couplant from the start of imaging (static imaging), through a typical procedure (dynamic imaging) and through longer duration procedures (prolonged imaging), to ensure desired image quality. This may be achieved by a variety of design features, including consistent thickness of the layers, increased concentration of couplant within the ultrashield, and/or with the addition of an accelerator membrane and/or accelerator device. These design features will be described in more detail herein.

Consistent Thickness of Layers

As mentioned previously, the couplant should be uniform across the tissue to provide a consistently uniform image. Any absence or unevenness typically inhibits the image and provides inadequate quality. This is particularly important during static imaging but is also important throughout the imaging stages.

Consistent thickness of the layers (e.g., probe contact layer 30, couplant layer 32, and/or body contact layer 34) can be achieved through precision of materials and engineering properties. In some embodiments, the probe contact layer 30 has a tolerance of 0.0001 inches, such as when the probe contact layer has a thickness of 0.0015 inches. In some embodiments, the couplant layer 32 has a tolerance of 0.001 inches, such as when the couplant layer 32 has a thickness of 0.050 inches. In some embodiments, the body contact layer 34 has a tolerance of 0.0005 inches, such as when the body contact layer 34 has a thickness of 0.0025 inches.

In addition, consistent material composition of the layers is desired and can also be achieved with precision of materials and engineering properties. In some embodiments, the couplant layer 32 comprises a hydrogel. In such embodiments, consistent water concentration is desired. It may be appreciated that desirable ultrasound images are achievable when the hydrogel has a water concentration of greater than 80%. In some embodiments, the hydrogel has a water concentration of 90%, such as with a tolerance of 3%. In other embodiments, the hydrogel has a water concentration of 95%, such as with a tolerance of 3%. In still other embodiments, the hydrogel has a water concentration of greater than 95%, such as 96%, 97%, 98%, 99%, or more. It may be appreciated that in some embodiments, the hydrogel has a water concentration of 85-90%, 85-95%, 90-95%, 95-96%, 95-97%, 95-98%, or 95-99%. It may be appreciated that the higher the fluid concentration in the couplant layer 32, the quicker the layers (e.g., probe contact layer 30, couplant layer 32, and/or body contact layer 34) of the ultrashield 10 become acoustic echogenic membranes. In some embodiments, the body contact layer 34 has a pore size in the range of 5-30 micrometers, 5-20 micrometers, 5-10 micrometers, 10-15 micrometers, 5-15 micrometers, 5 micrometers, 10 micrometers, 15 micrometers, 20 micrometers, or 30 micrometers, to name a few. Likewise, materials are chosen to be echogenic for ultrasound waves. And provide echogenic conductivity.

In some embodiments, sufficient or abundant couplant is provided from the start of imaging (static imaging), through a typical procedure (dynamic imaging) and through longer duration procedures (prolonged imaging) with the use of an accelerator membrane 100. The accelerator membrane 100 is a structure that assists in providing couplant to the ultrashield 10. In some embodiments, the accelerator membrane 100 is internal to the ultrashield 10, such as between layers of the ultrashield 10 and/or surrounding one or more particular layers of the ultrashield 10 integral with the ultrashield 10. In other embodiments, the accelerator membrane 100 is attached to the ultrashield 10. And in still other embodiments, the accelerator membrane 100 is separate from the ultrashield 10, yet its proximity provides couplant to the ultrashield 10.

Typically the accelerator membrane 100 comprises a structure having a sheet-like form. Thus, accelerator membrane 100 may be formed and/or cut into sheets, each having a thickness of less than 5 mm, typically 1-2 mm, 1-4 mm, 2-4 mm, or 3-4 mm. By its nature, the accelerator membrane 100 is moisture absorbent. In some embodiments, the membrane 100 is comprised of a cotton layer, a paper layer, a water absorbing hydrogel, or any suitable structure having water retention capability. In some embodiments, the accelerator membrane 100 has a foam structure, such as an open-cell structured foam. Open-cell-structured foams contain pores that are connected to each other and form an interconnected network that is relatively soft. Open-cell foams fill with the liquid that surrounds or is in contact with them. In some embodiments, the accelerator membrane 100 has a multi-pocket construction that contains fluid. In such embodiments, the pockets are optionally constructed with micropores which release fluid upon opening. In some embodiments, the membrane 100 is comprised of sodium polyacrylate, also known as waterlock. Sodium polyarcrylate is a sodium salt of polyacrylic acid creating a superabsorbent polymer that has the ability to absorb one hundred to one thousand times its mass in water. It has many favorable mechanical properties, including good mechanical stability, high heat resistance and strong hydration. It may be appreciated that the accelerator membrane may be comprised of a composite of plastic material with water retention capability. Typically, the accelerator membrane 100 is able to hold 5-10 mL of liquid, such as water. In some embodiments, the membrane 100 is able to hold 1-10 mL, 2-10 mL, 3-10 mL, 4-10 mL, 6-10 mL, 7-10 mL, 8-10 mL, or 9-10 mL of liquid. It may be appreciated that the membrane 100 is biocompatible with human tissue, such as skin, mucous membranes, blood, plasma, cells, etc.

As mentioned previously, in some embodiments the accelerator membrane 100 is internal to the ultrashield 10, such as between layers of the ultrashield 10 and/or surrounding one or more particular layers of the ultrashield 10 integral with the ultrashield 10.

Figure 7:
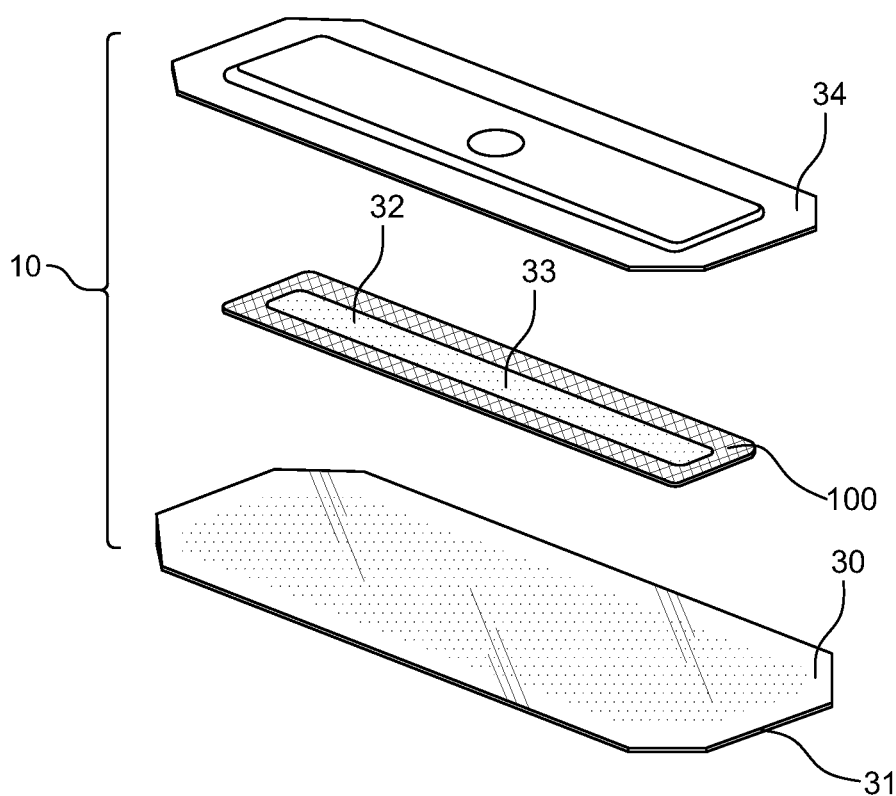
FIG. 7 illustrates an embodiment of an ultrashield having an accelerator membrane surrounding the couplant layer according to an example of the instant disclosure.

FIG. 7 illustrates an embodiment of an ultrashield 10 having an accelerator membrane 100 surrounding the couplant layer 32. Thus, the accelerator membrane 100 is internal to the ultrashield 10. In some embodiments, the accelerator membrane 100 does not significantly alter the overall dimensions of the ultrashield 10.

Figure 8:
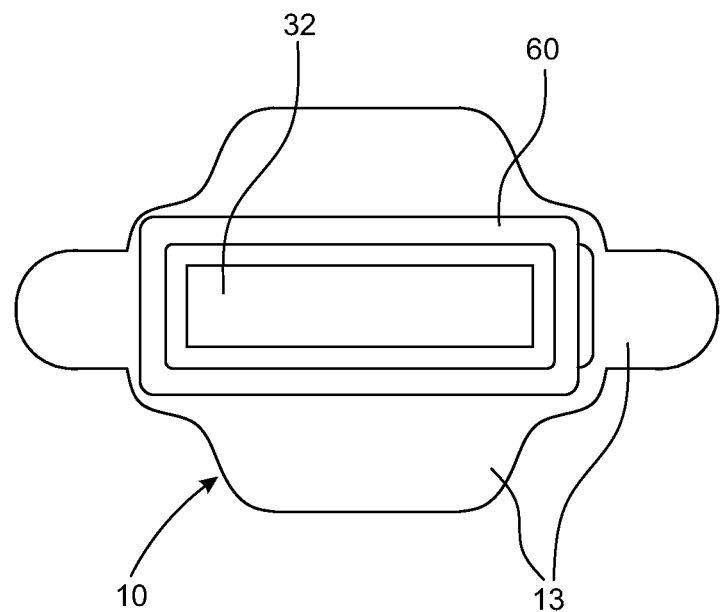
FIG. 8 illustrates another embodiment of an ultrashield having an accelerator membrane surrounding the couplant layer, wherein the ultrashield has tabs that are sized and configured to wrap around the probe according to an example of the instant disclosure.

FIG. 8 illustrates another embodiment of an ultrashield 10 having an accelerator membrane 100 surrounding the couplant layer 32. In this embodiment, the ultrashield 10 has tabs 13 that are sized and configured to wrap around the probe 14, beyond the faceplate 12, so as to ensure a complete seal.

Figure 9:
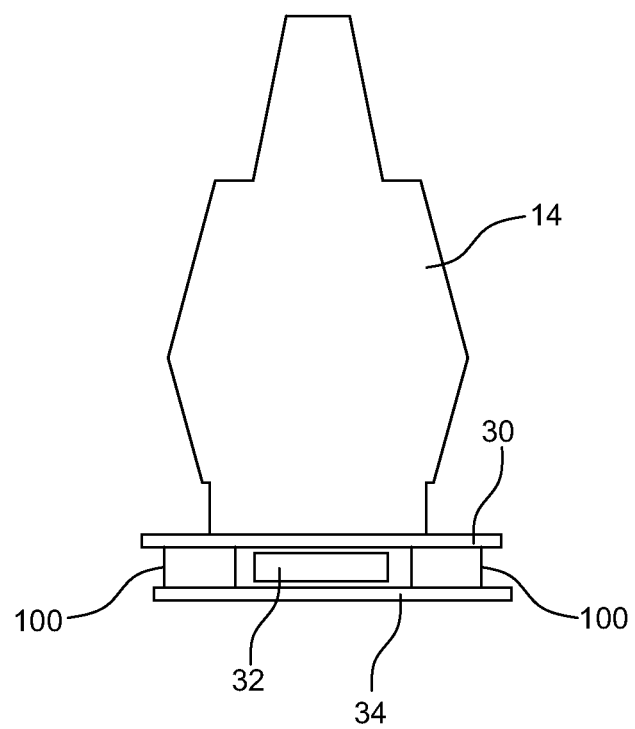
FIG. 9 provides a cross-sectional side view illustration of an ultrashield having an accelerator membrane surrounding the couplant layer, wherein the ultrashield is shown attached to a probe according to an example of the instant disclosure.

FIG. 9 provides a cross-sectional side view illustration of an ultrashield 10 having an accelerator membrane 100 surrounding the couplant layer 32, wherein the ultrashield 10 is shown attached to a probe 14. As shown, the accelerator membrane 100 is sandwiched between the probe contact layer 30 and the body contact layer 34 so as to contact both layers 30, 34 while the couplant layer 32 resides internally within the borders of the accelerator membrane 100.

It may be appreciated that the accelerator membrane 100 may be fully surrounding the couplant layer 32 or the accelerator membrane 100 may partially surround the couplant layer 32, such as bordering one side, two sides, or three sides of the couplant layer 32, bordering portions of one or more sides of the couplant layer 32, and/or bordering one or more corners of the couplant layer 32, or any combination. Typically, the accelerator membrane 100 does not significantly alter the overall dimensions of the ultrashield 10.

Thus, the accelerator membrane 100 serves as a reservoir of fluid that is able to immediately charge the couplant layer 32 with fluid, providing enhanced imaging from the start of use, and is able to continuously replenish the couplant layer 32 with fluid over time, enabling extended imaging due to the additional capacity of available fluid.

Figure 10C:
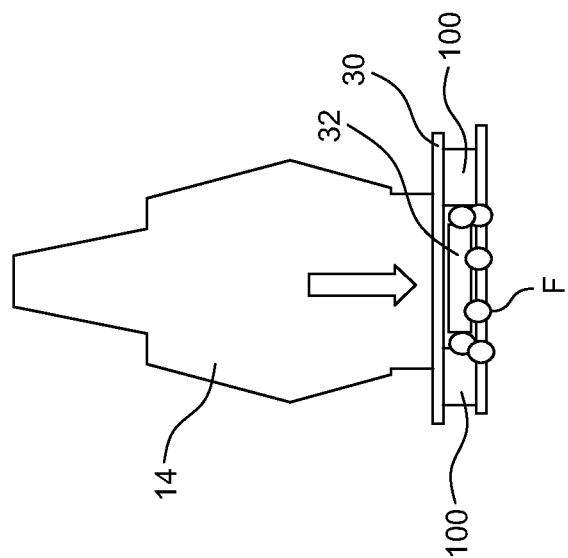
FIGS. 10A-10C illustrate priming of the ultrashield prior and during use according to an example of the instant disclosure.
Figure 10B:
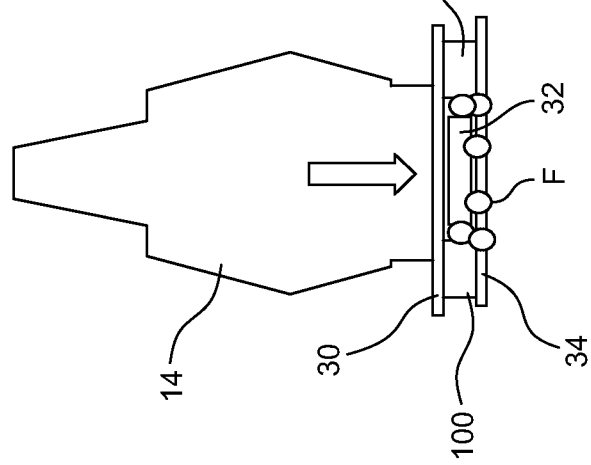
Figure 10A:
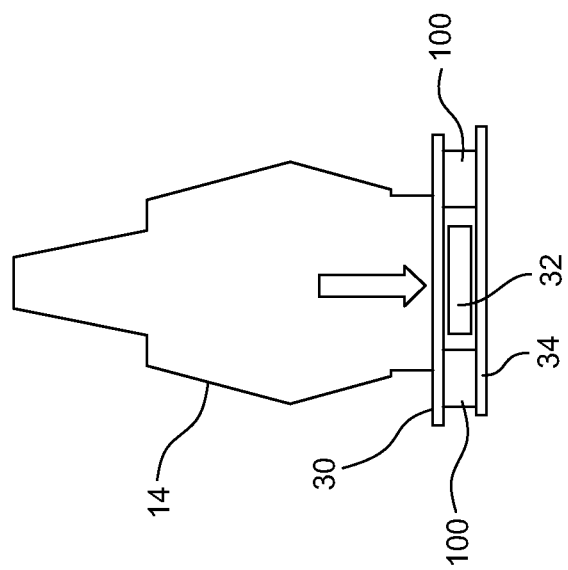

FIGS. 10A-10C illustrate such priming of the ultrashield prior and during use. FIG. 10A illustrates the pre-moistened accelerator membrane 100 immediately charging the couplant layer 32 with fluid. FIG. 10B illustrates the fluid F wetting the body contact layer 34 and surface of the patient upon use. During dynamic imaging, the accelerator membrane 100 functions as an additional lubricant. When the probe 14 and attached ultrashield 10 is advanced, the accelerator membrane 100 dispenses fluid F ahead of the actual imaging process due to its strategic placement. This will provide superior enhancement of imaging by wetting the tissue prior to imaging, such as illustrated in FIG. 10C. The wet tissue surface and the design of the patient contact layer further enhances the movement of the probe 14. The fluid F will wet the tissue and reduce overall friction between the tissue and the patient contact layer.

Figures 12A, 12B:
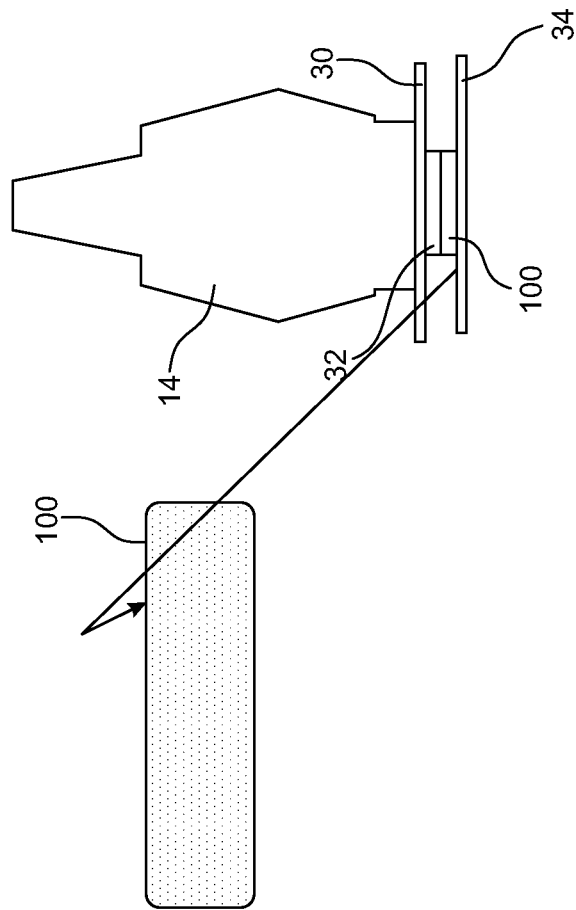
FIGS. 12A-12B illustrate an embodiment of an accelerator membrane having the form of a sheet that is positioned adjacent a couplant layer, so that the accelerator membrane is disposed between the couplant layer and the body contact layer according to an example of the instant disclosure.
Figure 11:
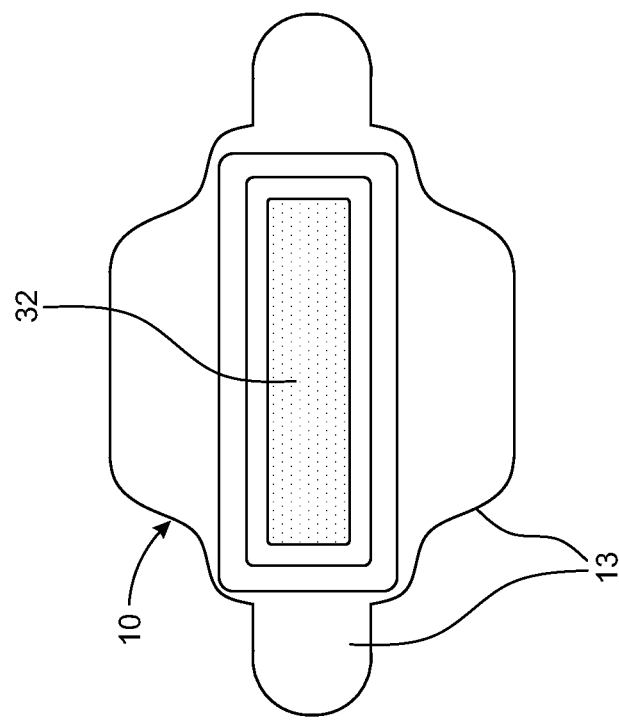
FIG. 11 illustrates another embodiment wherein the accelerator membrane is internal to the ultrashield according to an example of the instant disclosure.

FIG. 11 illustrates another embodiment wherein the accelerator membrane 100 is internal to the ultrashield 10. In this embodiment, the accelerator membrane 100 has the form of a sheet (as shown in FIG. 12A) that is positioned adjacent the couplant layer 32 (as shown in FIG. 12B), so that the accelerator membrane 100 is disposed between the couplant layer 32 and the body contact layer 34. In this embodiment, the accelerator membrane 100 has the same length and width as the couplant layer 32 so as to align with the couplant layer 32. However, it may be appreciated that in other embodiments the dimensions of the accelerator membrane 100 and couplant layer 32 do not match. It may be appreciated that in some embodiments the accelerator membrane 100 has the same thickness as the couplant layer 32 and in other embodiments the thicknesses differ. In one embodiment, the thickness of the accelerator membrane 100 is greater than the thickness of the couplant layer 32. Since the accelerator membrane 100 is comprised of a compressible material, when pressure is applied during imaging, the accelerator membrane 100 will dispense couplant liquid, such as water, and will reduce in thickness, optionally becoming thinner than the couplant layer 32. The dispensed fluid will be absorbed by the couplant layer 32 which enhances the imaging properties of the couplant layer 32.

It may also be appreciated that in other embodiments, the accelerator membrane 100 is disposed between the couplant layer 32 and the probe contact layer 30. In either case, the accelerator membrane 100 further bolsters the capability of the ultrashield 10 to increase a rapid start and to enable longer imaging capability.

Again, the accelerator membrane 100 serves as a reservoir of fluid that is able to immediately charge the couplant layer 32 with fluid, providing enhanced imaging from the start of use, and is able to continuously replenish the couplant layer 32 with fluid over time, enabling extended imaging due to the additional capacity of available fluid.

Figure 13C:
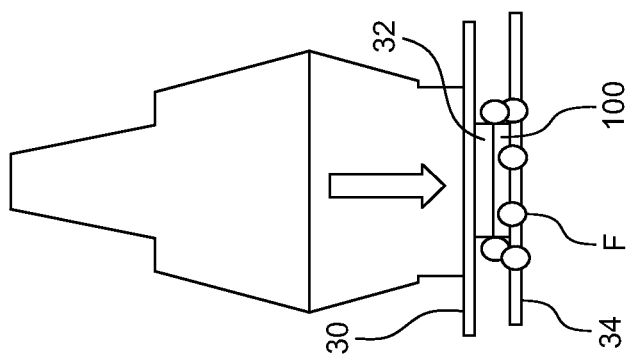
FIGS. 13A-13C illustrate priming of the ultrashield of FIG. 11 prior and during use according to an example of the instant disclosure.
Figure 13B:
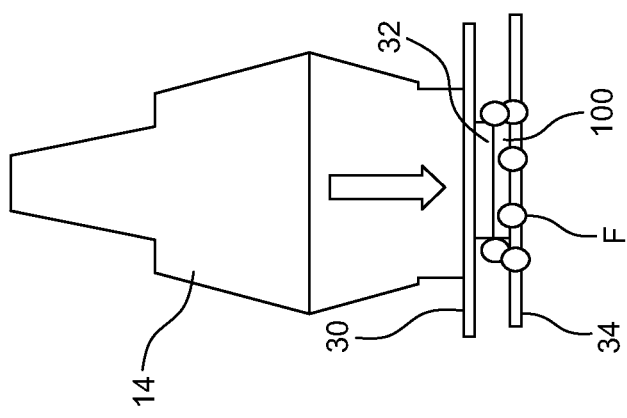
Figure 13A:
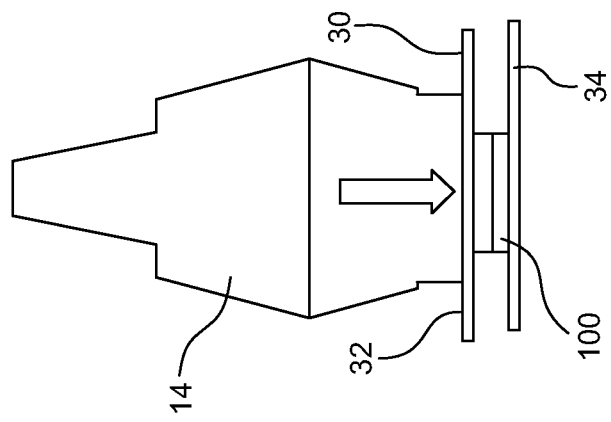

FIGS. 13A-13C illustrate such priming of the ultrashield 100 of FIG. 11 prior and during use. FIG. 13A illustrates the pre-moistened accelerator membrane 100 immediately charging the couplant layer 32 with fluid F. FIG. 13B illustrates the fluid F is wetting the body contact layer 34 and surface of the patient upon use. During dynamic imaging, the accelerator membrane 100 functions as an additional lubricant; when the probe 14 and attached ultrashield 10 is advanced, the accelerator membrane 100 dispenses fluid ahead of the actual imaging process due to its strategic placement. This will provide superior enhancement of imaging by wetting the tissue prior to imaging, such as illustrated in FIG. 13C. Again, the wet tissue surface and the design of the patient contact layer further enhances the movement of the probe 14. The fluid will wet the tissue and reduce overall friction between the tissue and the patient contact layer.

Figure 14C:
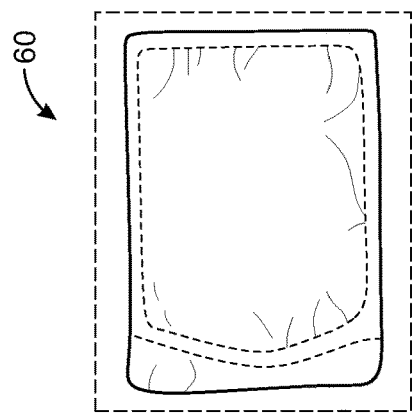
FIG. 14C illustrates a protective pouch or sleeve for packaging the ultrashield and optionally one or more additional accelerator membranes according to an example of the instant disclosure.
Figure 14B:
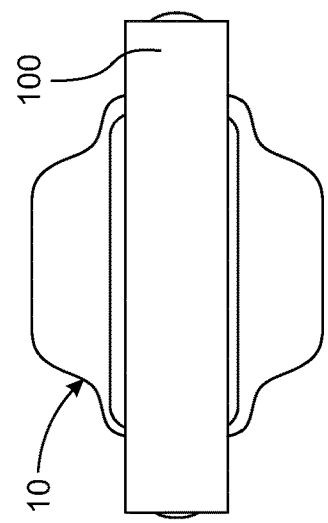
FIG. 14B illustrates an accelerator membrane removably fixed to the ultrashield according to an example of the instant disclosure.
Figure 14A:
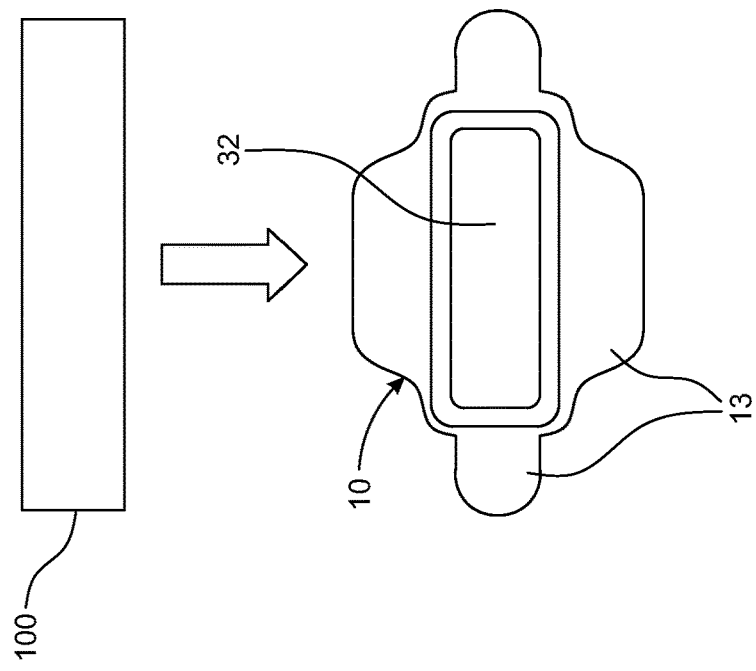
FIG. 14A illustrates an embodiment of an ultrashield and a separate accelerator membrane according to an example of the instant disclosure.

In some embodiments, the accelerator membrane 100 is external to the ultrashield 10. For example, FIG. 14A illustrates an embodiment of an ultrashield 10 and a separate accelerator membrane 100. In this embodiment, the accelerator membrane 100 has the form of a sheet, typically sufficiently sized to cover the couplant layer 32. In some embodiments, the accelerator membrane 100 includes an adhesive or another fixation mechanism, such as a pressure-sensitive adhesive, which is able to attach the accelerator membrane 100 to the ultrashield, such as illustrated in FIG. 14B. Typically, the accelerator membrane 100 is attached to the body contact layer 34 and is removed prior to use. Such adherence of the accelerator membrane 100 to the body contact layer 34 ensures that the body contact layer 34 is pre-wetted and ready to immediately exhibit a desirable image from the start of the procedure upon removal of the accelerator membrane 100. It may be appreciated that the ultrashield 10 is typically packaged in a protective pouch or sleeve 60 (e.g., as shown in FIG. 14C) which extends over the ultrashield 10 to protect the ultrashield 10 prior to use. As shown, the protective sleeve 60 encases the ultrashield 10 and adhered accelerator membrane 100 so as to resist or prevent water vapor loss or loss of couplant. This provides an extended shelf-life and ensures that the ultrashield 10 is ready for use when the protective sleeve 60 is removed.

Figure 15:
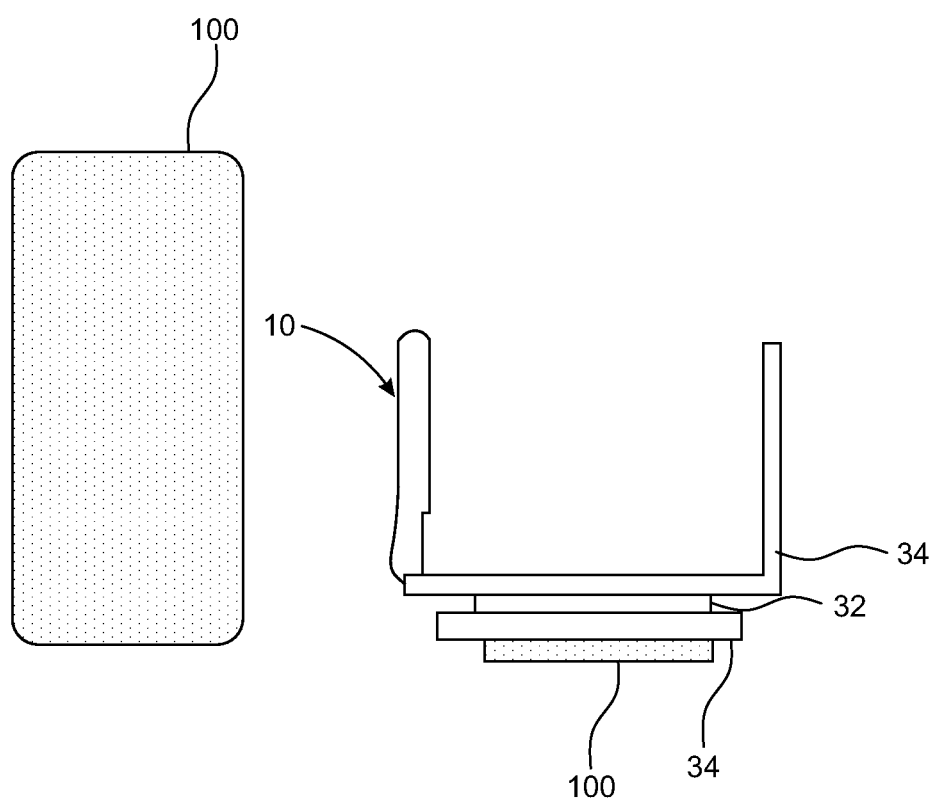
FIG. 15 illustrates an embodiment wherein the accelerator membrane is external to the ultrashield and resides loose inside the packaging, such as inside the protective sleeve according to an example of the instant disclosure.

In some embodiments, as illustrated in FIG. 15, the accelerator membrane 100 is external to the ultrashield 10 and resides loose inside the packaging, such as inside the protective sleeve 60. In such embodiments, the accelerator membrane 100 may reside in various locations within the protective sleeve 60, however in preferred embodiments the accelerator membrane 100 is positioned in contact with the body contact layer 34. Such contact of the accelerator membrane 100 with the body contact layer 34 ensures that the body contact layer 34 is pre-wetted and ready to immediately exhibit a desirable image from the start of the procedure upon removal of the ultrashield 10 from the protective sleeve 60.

In other embodiments, the accelerator membrane 100 is external to the ultrashield 10 and is attached to or integral with the packaging. In some embodiments, the packaging, such as a protective sleeve 60, includes a location or a receptacle for the accelerator membrane 100. The receptacle is arranged within the sleeve 60 so that the accelerator membrane 100 is resides near, adjacent and optimally against the ultrashield 10 while the ultrashield 10 is positioned within the sleeve 60. Thus, the accelerator membrane 100 is able to immediately charge the couplant layer 32 of the ultrashield 10 with fluid, providing enhanced imaging from the start of use. In addition, the accelerator membrane 100 is easily accessible later in the imaging procedure. For example, the protective sleeve 60 may be arranged so that the attached accelerator membrane 100 is exposed and accessible. When the ultrashield 10 is attached to the probe 14, the probe 14 and attached ultrashield 10 may be pressed against the accelerator membrane 100 so that the accelerator membrane 100 is rehydrated. This action is analogous in many ways to the pressing of a rubber stamp against a stamp pad so as to re-ink the rubber stamp. Thus, if the ultrasound image degrades, such as appearing hazy, the ultrashield 10 can be rehydrated by pressing against the accelerator membrane 100 which is conveniently accessible by the provided packaging. Therefore, the couplant layer 32 is able to be continuously replenished with fluid over time, enabling extended imaging due to the additional capacity of available fluid. This may be particularly useful during long imaging processes, such as for deep abdomen imaging.

Figure 16A:
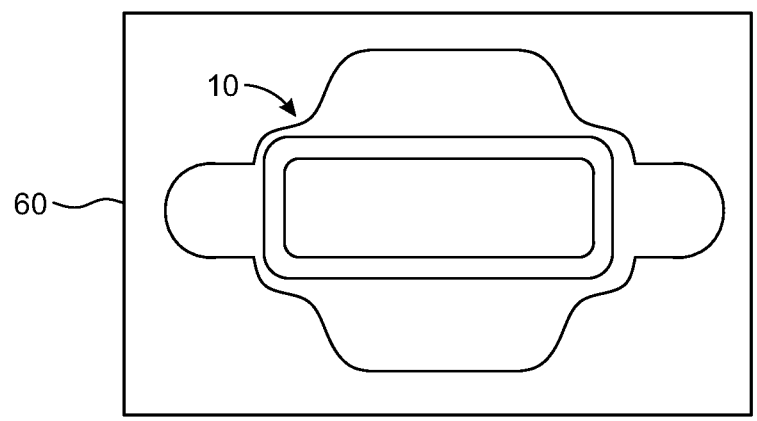
FIGS. 16A-16B illustrate a protective sleeve for packaging an ultrashield along with an ultrashield according to an example of the instant disclosure.
Figure 16B:
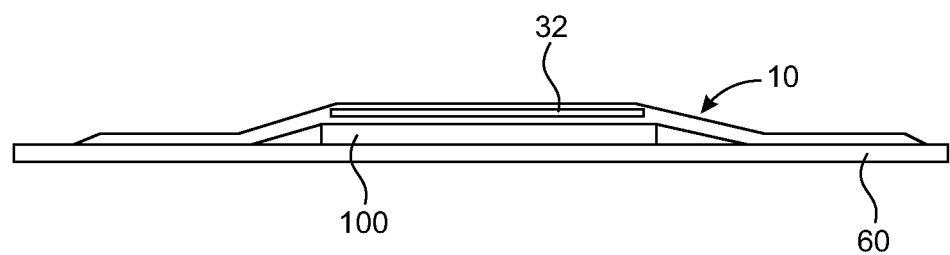

FIGS. 16A-16B illustrate a protective sleeve 60 for packaging an ultrashield along with an ultrashield 10. FIG. 16A illustrates a top view of an embodiment of an ultrashield 10 positioned upon a protective sleeve 60. FIG. 16B provides a side view illustration of this embodiment. Here, as shown, the accelerator membrane 100 is mounted on the protective sleeve 60. The ultrashield 10 is then positioned over the protective sleeve 60 so that the couplant layer 32 aligns with the accelerator membrane 100. This allows wetting of the couplant layer 32 so that the ultrashield 10 is charged and ready for immediate use upon removal of the ultrashield 10 from the protective sleeve 60.

Figure 17A:
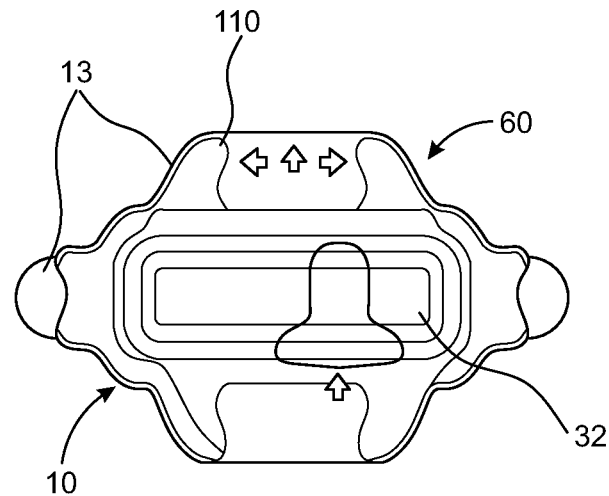
FIGS. 17A-17B illustrate an embodiment of a protective sleeve having a receptacle to which is affixed an accelerator membrane and removable ultrashield according to an example of the instant disclosure.
Figure 17B:
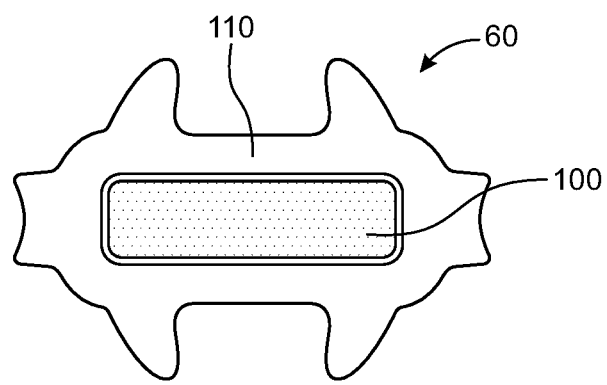

FIGS. 17A-17B illustrate an embodiment of a protective sleeve 60 having a receptacle 110 to which is affixed the accelerator membrane 100 and removable ultrashield 10. FIG. 17A illustrates a portion of the sleeve 60 having the ultrashield 10 removably attached to the receptacle 110. In this embodiment, the ultrashield 10 has tabs 13 which are configured to wrap around the probe 14. Thus, the receptacle 110 has matching areas to which the tabs 13 are removably attached. In this embodiment, the ultrashield 10 is adhered to the receptacle 110 with a layer of adhesive. FIG. 17B illustrates the receptacle 110 after the ultrashield 10 is removed. The accelerator membrane 100 remains affixed to the receptacle 110, available for rewetting the ultrashield, such as in the stamp pad manner as described above. It may be appreciated that the accelerator membrane 100 can be used in other manners, such as manually pressing the accelerator membrane 100 against the ultrashield 10, such as with one's hand, or applying the accelerator membrane 100 to any suitable surface, including tissue of the patient.

Packaging Material

Figure 18:
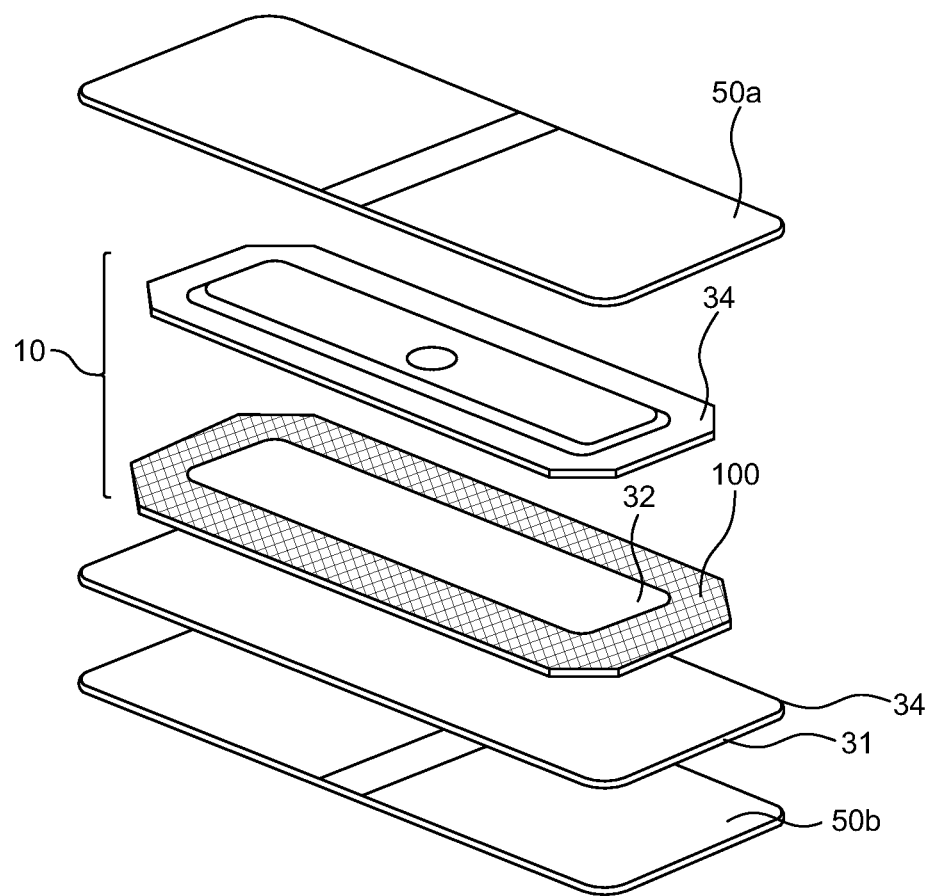
FIG. 18 illustrates an embodiment of an ultrashield between packaging layers in an expanded view according to an example of the instant disclosure.

The ultrashield 10 is packaged so as to reduce or eliminate evaporation of couplant from the couplant layer 32 and the accelerator membrane 100. Thus, such packaging will assist in increasing shelf-life and ensure that the ultrashield 10 is desirably functioning when removed from the packaging for use. In some embodiments, as illustrated in FIG. 18, the ultrashield 10 is disposed between packaging layers 50a, 50b. The packaging layers 50a, 50b are sized and configured to encase the ultrashield 10. Such arrangement is typically utilized with the accelerator membrane 100 internal or integral with the ultrashield 10. In most embodiments, the probe contact layer 30 has an adhesive 31 which adheres the probe contact layer to the packaging layer 50b. In some embodiments, when the packaging layer 50b is removed for use, the same adhesive 31 is then used to adhere the ultrashield 10 to the probe 14. The other packaging layer 50a is adhered to the body surface layer 34 with an adhesive which remains on the packaging layer 50a when the packaging layer 50a is removed. Thus, the body surface layer 34 is free of adhesive when ready for use. The ultrashield 10 plus packaging layers 50a, 50b are then packaged in a packaging sleeve 60.

Figure 19:
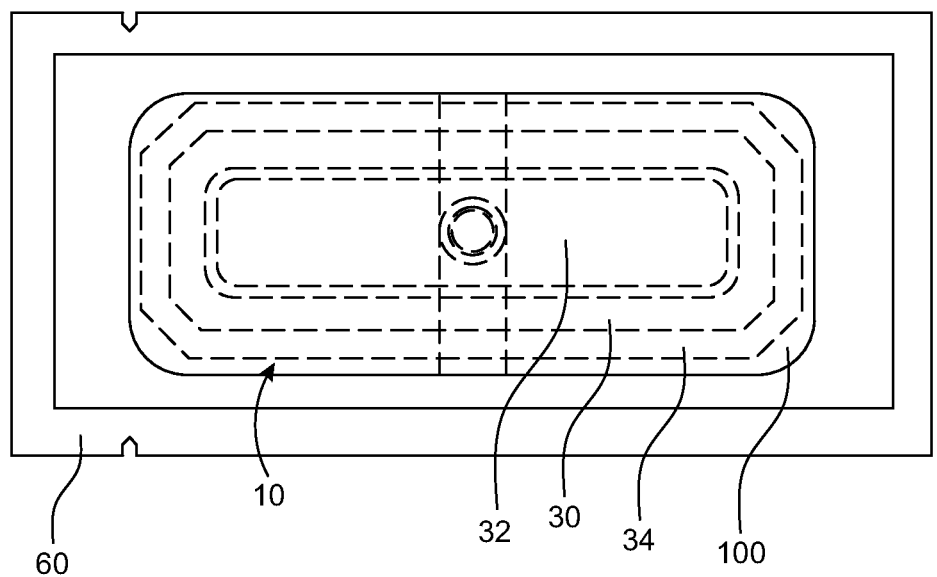
FIG. 19 illustrates an embodiment of a packaging sleeve having an ultrashield disposed therein according to an example of the instant disclosure.

FIG. 19 illustrates an embodiment of a packaging sleeve 60 having an ultrashield 10 disposed therein. The sleeve 60 protects the ultrashield 10 during transport and storage and optionally holds an accelerator membrane 100, such as loose within the sleeve 60 or attached to the sleeve 60. It may be appreciated that the ultrashield 10 may contain or not contain one or more accelerator membranes 100 and the packaging sleeve 60 may contain or not contain one or more accelerator membranes 100. Thus, in some embodiments, the ultrashield 10 may contain an accelerator membrane 100 and be packaged with an additional accelerator membrane 100. Likewise, a plurality of accelerator membranes 100 may be located within or outside of the ultrashield 10.

As mentioned, the packaging sleeve 60 is comprised of a material, which reduces water vapor transmission or loss of couplant. In some embodiments, the packaging sleeve 60 allows minimal to no transmission of water vapor or couplant. This ensures the presence of moisture in the ultrashield 10 when the packaging sleeve 60 is opened for use of the ultrashield 10. It may be appreciated that, alternatively or in addition, the packaging layers 50a, 50b (when present) may be comprised of a material which reduces water vapor transmission or loss of couplant. Water or vapor transmission can be characterized by the moisture vapor transmission rate (MVTR) which is the rate at which water vapor transfers through a given substance. MVTR can be tested and evaluated for various materials. In some embodiments, the MVTR g/m$^2$ 24 hours, 38° C., 90% relative humidity (rh) is less than 1. Typical MVTR for different acceptable package materials are shown in the following table:

TABLE ONE

| MATERIAL | MVTR g/m$^2$ 24 hours 38° C. 90% rh | OXYGEN TRANSMISSION RATE* cc/m$^2$ 24 hours at atmospheric temperature and pressure |
|---|---|---|
| Polyester Film/Aluminium Foil/low density polyethylene (LDPE) Film Laminates | less than 0.01 | less than 0.006 |
| 12 Micron Metallised Polyester Film | 0.7 to 2.0 | 2.0 |
| 12 Micron Metallised PET/Adhesive/50 Mic LPDE Film | 0.4 | 0.6 |
| Polyester Film (12 Micron) | 40 | 105 |
| BOPP Film (12 Micron) | 355 | 42 |
| CPP Film (30 Micron) | 11 | 4800 |
| LDPE Film | 18 | 8000 |

Due to the low water vapor transmission of the packaging material, the sleeve 60 is not able to be steam sterilized. Thus, in some embodiments, radiation (gamma) or electron beam sterilization is used. Therefore, the packaging material is capable of radiation or electron beam sterilization without disintegration. Likewise, ultrashield 10 is comprised of resilient materials as well.

Probe Cover

As mentioned previously in relation to FIGS. 3A-3B, in some embodiments the ultrashield 10 is used with a probe cover 20. The probe cover 20 provides a removable barrier between the probe 14 and the individual patient which will prevent infectious particles from being transmitted to different patients due to inadequate cleanings of the probe between uses. Such a barrier between the patient and the probe 14 (that is exchanged between probe uses) is particularly important for many probes 14 which have crevices and contours that have been found to be very difficult to definitively clean, leading to an increased risk of spreading infectious particles. It may be appreciated that the embodiments described herein in relation to components incorporated in, used with and/or packaged with an ultrashield 10 are applicable to an ultrashield 10 combined with a probe cover 20.

Figure 20:
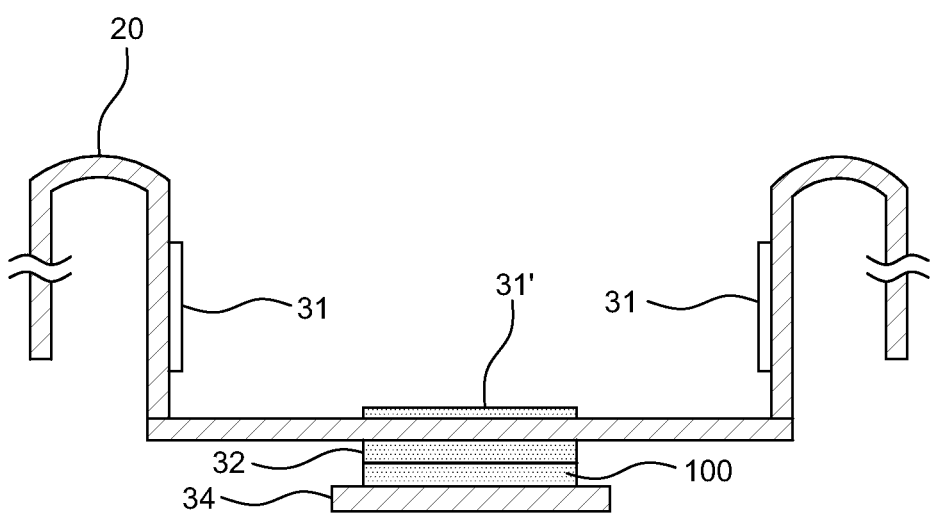
FIG. 20 is a schematic illustration of an embodiment of a probe cover having an ultrashield according to an example of the instant disclosure.

FIG. 20 is a schematic illustration of an embodiment of a probe cover 20 having an ultrashield 10. In this embodiment, the ultrashield 10 comprises a couplant layer 32 and a body surface layer 34 which are built into a bottom portion or surface of the probe cover 20. Optionally, an accelerator membrane 100 may be built in as well in a manner similar to above as described in relation to the ultrashield 10. In this embodiment, the couplant layer 32 comprises a hydrogel which captures the couplant. The skin contact layer 34 comprises a filtration membrane that controls the amount and rate of liquid being delivered. It also has low co-efficient of friction and glides easily on the patient skin. It may be appreciated that in this embodiment, couplant layer 32 is directly adjacent the probe cover 20, wherein a separate probe contact layer 30 is not present. As such the probe cover 20 acts as the probe contact layer 30. The probe cover 20 is configured to extend over a probe 14 so that the ultrashield 10 is aligned with the faceplate 12 of the probe 14. Typically, the probe cover 20 includes adhesive 31 along a portion of its inner walls or surfaces to hold the cover 20 snugly to the probe 14. In some embodiments, the probe cover 20 also includes an adhesive 31' disposed along the inside of the probe cover 20 at a location so as to adhere the probe cover 20 directly to the faceplate 12 of the probe 14. It may be appreciated that the adhesive 31, 31' may cover a variety of surfaces of the probe cover 20 to assist in adhering the ultrashield 10 to the probe 14.

It may be appreciated that in some embodiments the ultrashield 10 is separate from the probe cover 20 and can be adhered to a surface of the probe cover 20 for use. Thus, rather than adhering the probe contact layer 30 directly to the probe 14, the probe contact layer 30 is adhered to the probe cover 20. This allows the user to utilize the ultrashield 10 with any probe cover 20 or similar device.

Retainer Module

As mentioned previously, in some embodiments the ultrashield 10 is used with a retainer module 300. The retainer module 300 provides some of the same features as the probe cover 20. In particular, an ultrashield 10 can be adhered to the retainer module 300 rather than directly to the probe 14. The probe 14 is then easily coupled with the retainer module 300. Even though adherence to the faceplate 12 does not impact the probe 14, it is sometimes preferred to have no contacting materials so as to avoid any potential risk to the probe 14 under any circumstances. During use, the probe 14 typically endures a clean, scrub, soak, and rinse process to eliminate any potential adhesive residue, etc. If this process is eliminated, the life of the probe 14 is potentially extended.

Figure 21A:
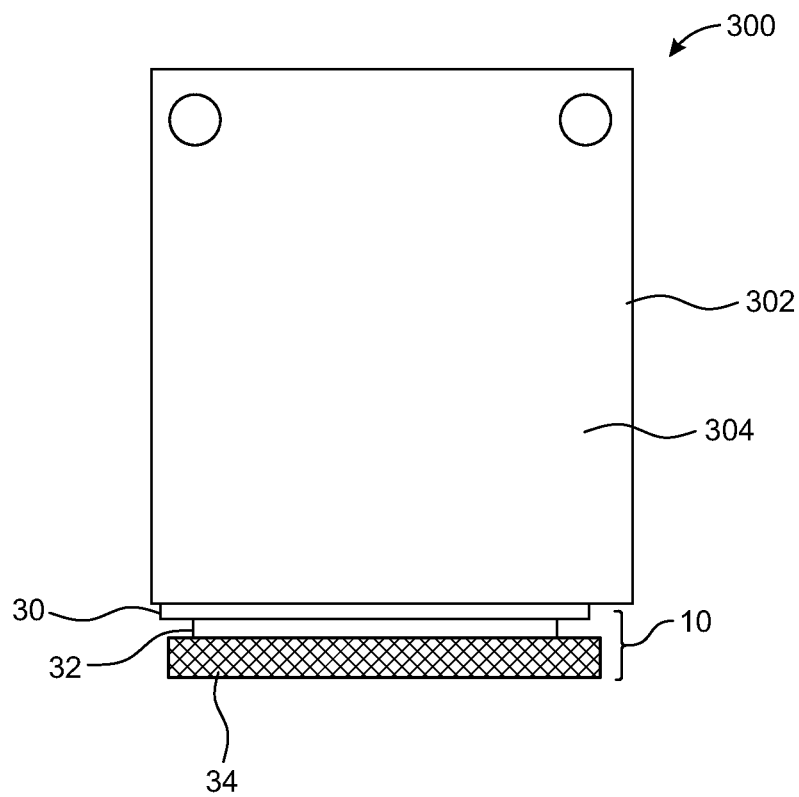
FIGS. 21A-21B illustrate an embodiment of a retainer module according to an example of the instant disclosure. In particular, FIG. 21A provides a front view of the embodiment of the retainer module and FIG. 21B provides a side view of the retainer module according to an example of the instant disclosure.
Figure 21B:
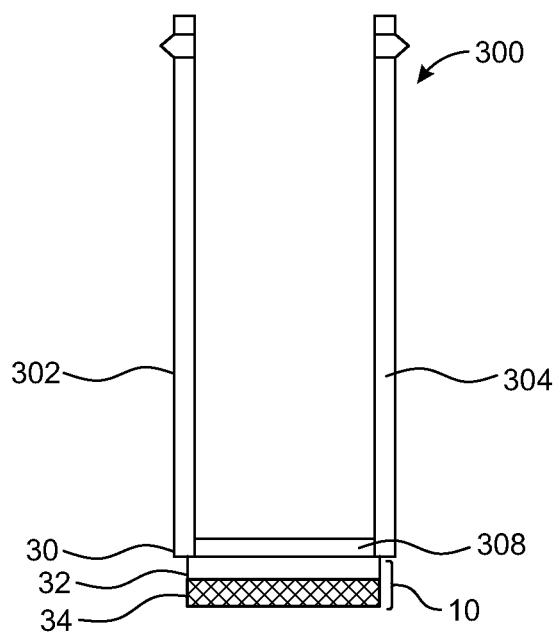

The retainer module 300 provides a quick and efficient way of attaching the ultrashield 10 to the probe 14 without adhesion. FIGS. 21A-21B illustrate an embodiment of a retainer module 300. In particular, FIG. 21A provides a front view of the embodiment of the retainer module 300 and FIG. 21B provides a side view. In this embodiment, the retainer module 300 comprises a structure 302 having at least three sides, a front side 304, a back side 306 and a bottom side 308. Thus, the sides 304, 306, 308 are arranged in a U shape, as shown in FIG. 21B. The front side 304 and the back side 306 are spaced apart the width of the head of the probe 14 so that the head of the probe 14 is able to be inserted therebetween. Typically, the front side 304 and the back side 306 are positioned to "hug" the probe or mate tightly or closely. The head of the probe 14 is inserted sufficiently so that the faceplate 12 resides against the bottom side 308.

Figure 22A:
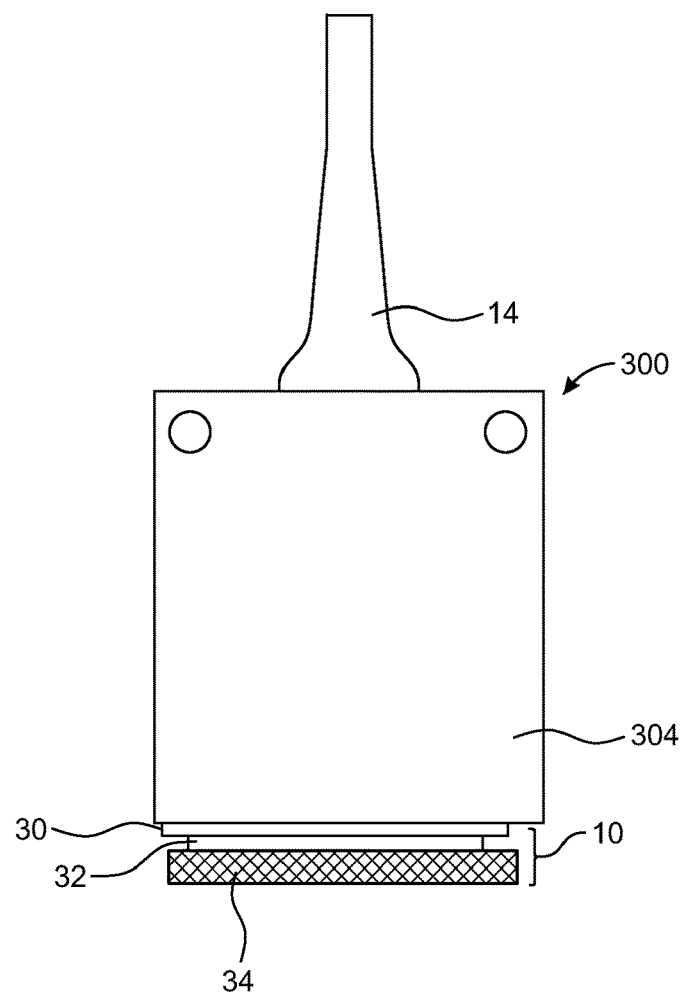
FIGS. 22A-22C illustrate insertion of a head of a probe into the embodiment of the retainer module of FIGS. 21A-21B according to an example of the instant disclosure.
Figure 22B:
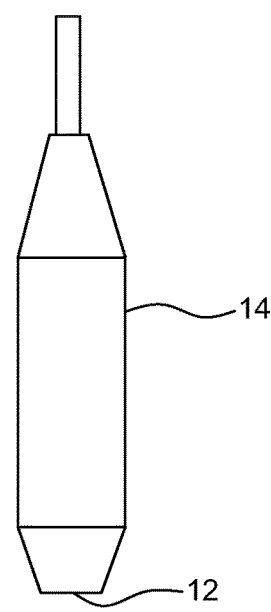
Figure 22C:
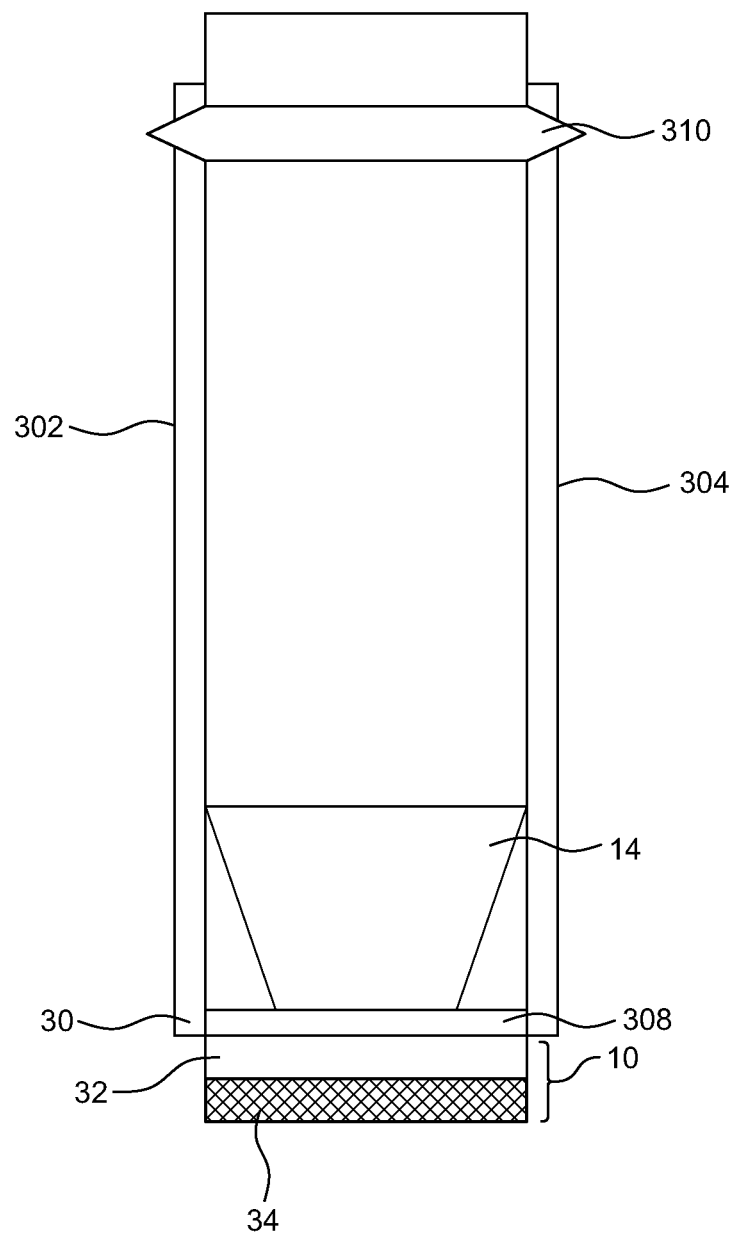

FIGS. 22A-22C illustrate such insertion. In particular, FIG. 22A provides a front view of the embodiment of the retainer module 300 with the probe 14 inserted therein. FIG. 22B illustrates the probe 14 itself. It may be appreciated that probes 14 may be available in a variety of shapes. Therefore, in some embodiments the retainer module 300 is custom configured to mate with a particularly shaped probe 14, and in other embodiments the retainer module 300 is adaptable to various shaped probes 14. FIG. 22C illustrates a side view of the retainer module 300 having the head of the probe 14 inserted therein so that the faceplate 12 resides against the bottom side 308. In this embodiment, the retainer module 300 is further secured to the probe 14 with a coupling mechanism 310 that couples the front side 304 and back side 306 together at a position spaced a distance from the bottom side 308. In this embodiment, the coupling mechanism 310 comprises a latch which may be either flexible or rigid. It may be appreciated that other mechanisms may be used including bands, hooks, links, strips, cords, etc.

An ultrashield 10 is either affixed to or integral with the retainer module 300. In particular, the ultrashield 10 is disposed along the bottom side 308. Therefore, the probe 14 is able to image through the faceplate 12, the bottom side 308 and/or the ultrashield 10 while in use. In some embodiments, the ultrashield 10 is adhered to the bottom side 308 with adhesive. In such instances, the bottom side 308 is comprised of a suitable material that has a low level of attenuation co-efficient and provides minimal or no diminishment of ultrasound wave transmission. In some embodiments, the bottom side 308 is comprised of the same or similar material as that of the probe contact layer 30 described herein above. For example, in some embodiments, the bottom side 308 has a thickness in the range of 0.010 to 0.060 inches, more particularly 0.030 to 0.060 inches. Similarly, in some embodiments, the bottom side 308 has a thickness of less than or equal to 0.060 inches, less than or equal to 0.050 inches, less than or equal to 0.040 inches, or less than or equal to 0.020 inches. In some embodiments, the bottom side 308 is comprised of quartz or a polymer such as polyethylene, polyurethane, polypropylene, polyester, ethylene vinyl acetate, polyvinyl chloride, or the like.

In other embodiments, the bottom side 308 is comprised of a predesigned receptacle for securely receiving the ultrashield 10 without the use of adhesive. In such embodiments, the ultrashield 10 is in direct contact with the faceplate 12 when the ultrasound wand is properly inserted into the retainer module 300. In each of these instances, the retainer module 300 serves as a "quick connect" way to securely connect the ultrashield 10 to the probe 14 without adhesion. The retainer module 300 can be just as easily disconnected to decouple from the probe 14.

It may be appreciated that the retainer module 300 may be constructed from a variety of materials, such as polycarbonate, acrylonitrile butadiene styrene, Polycarbonate/Acrylonitrile Butadiene Styrene (a blend of PC and ABS providing high processability of ABS with the excellent mechanical properties, impact and heat resistance of PC), nylon, silicone, to name a few. In some embodiments, the retainer module 300 is injection molded, blow molded, or thermoformed.

It may also be appreciated that the accelerator membrane 100 may be utilized in combination with the retainer module 300, such as in any of the ways described herein in relation to the ultrashield 10. Thus, the accelerator membrane 100 may reside within the ultrashield 10 or external to the ultrashield 10 as described in various embodiments herein. In addition, the retainer module 300 may be used in combination with an accelerator device 200 as described herein below.

Additional Embodiments

In some embodiments, an accelerator device 200 is used in combination with or in addition to an accelerator membrane to provide sufficient or abundant couplant from the start of imaging (static imaging), through a typical procedure (dynamic imaging) and through longer duration procedures (prolonged imaging), to ensure desired image quality.

FIGS. 23A-23B illustrate a probe 14 and an accelerator device 200 that is positionable at least partially around the probe 14 so as to deliver couplant 37 and/or other materials to the surface upon which the probe 14 is placed. In this embodiment, the accelerator device 200 comprises a flexible reservoir 202 fillable with couplant 37, such as water, oil, gel, glycerin, or any suitable couplant material. The reservoir 202 has the shape of two arms 204a, 204b connected on one side so as to create a continuous reservoir within. The opposite side is open, so as to create an "open mouth" shape, which allows the accelerator device 200 to be slipped over and around the distal end of a probe 14 so that each arm 204a, 204b straddles the probe 14, and therefore faceplate 12 of the probe 14 (as indicated by arrows). The accelerator device 200 includes one or more ports 206 which allow delivery of the couplant 37 from the accelerator device 200. In this embodiment, the ports 206 are disposed along a bottom surface of the accelerator device 200, particularly along a bottom surface of the arms 204a, 204b, so that the couplant 37 is deliverable directly to the surface upon which the probe 14 is positioned, such as the skin or tissue of the patient. In some embodiments, the couplant 37 is delivered at a flow rate of 0.5-3 ml/hr. In this embodiment, the accelerator device 200 is comprised of a flexible material which allows the arms 204a, 204b to be compressed which forces the couplant 37 through the ports 206 and onto the surface upon which the probe 14 is positioned. In this embodiment, the ports 206 are comprised of one-way valves, such as duckbill valves, which allow couplant 37 to pass out of the reservoir 202 when pressure is applied to the arms 204a, 204b and resists passage of couplant 37 when pressure is relieved. This reduces or prevents any excess couplant 37 from flowing through the ports 206, particularly when undesired during the procedure. Thus, the user is able to hold the probe 14 in a conventional manner, moving the faceplate 12 along a surface. When additional couplant 37 is desired on the surface, the user simply presses on the reservoir 202 which is readily available at least partially surrounding the probe 14 in close proximity to the user's hand. A desired amount of couplant 37 is expelled in close proximity to the faceplate 12 to ensure consistent imaging, the quantity expelled being correlated to the amount of pressure and/or the number of compressions of the reservoir 202 by the user.

FIGS. 24A-24B provide a top view of the probe 14 and accelerator device 200 of FIGS. 23A-23B. As illustrated, the accelerator device 200 comprises a flexible reservoir 202 having the shape of two arms 204a, 204b connected on one side to create a continuous reservoir within. The opposite side is open, so as to create an "open mouth" shape, which allows the accelerator device 200 to be slipped over and around the distal end of a probe 14 so that each arm 204a, 204b straddles the probe 14, and therefore faceplate 12 of the probe 14 (as indicated by arrows). The arms 204a, 204b are flexible to flex outwardly to allow the probe 14 to be inserted therebetween. In some embodiments, the arms 204a, 204b flex or bend up to one inch from its natural resting position. The accelerator device 200 provides recoil strength to hold the arms 204a, 204b against the inserted probe 14. Thus, in this embodiment, the accelerator device 200 is held on the probe 14 by friction and/or gripping force.

Figure 25:
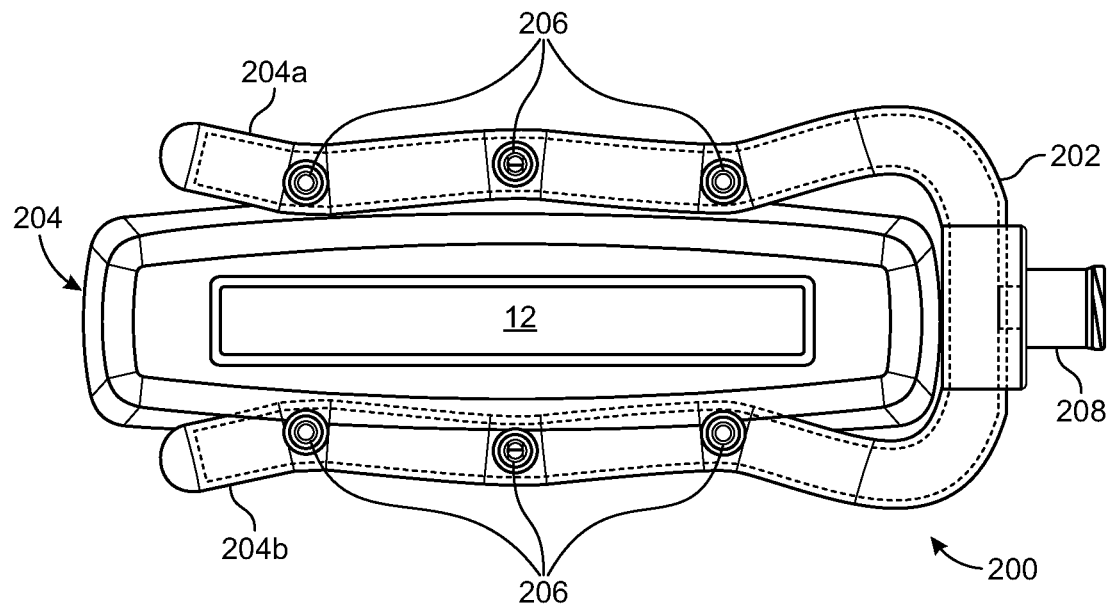
FIG. 25 illustrates an embodiment of an accelerator device positioned on a probe according to an example of the instant disclosure.

FIG. 25 illustrates the accelerator device 200 positioned on the probe 14. In this embodiment, the arms 204a, 204b extend along opposite sides of the head of the probe 14, reaching approximately the full width of the head of the probe 14. In this embodiment, the side of the probe 14 rests against the portion of the accelerator device 200 connecting the arms 204a, 204b. However, it may be appreciated that the accelerator device 200 may be advanced any distance onto the probe 14. Likewise, the arms 204a, 204b may be of any desired length including jointly wrapping around all four sides of the head of the probe 14.

Figure 26:
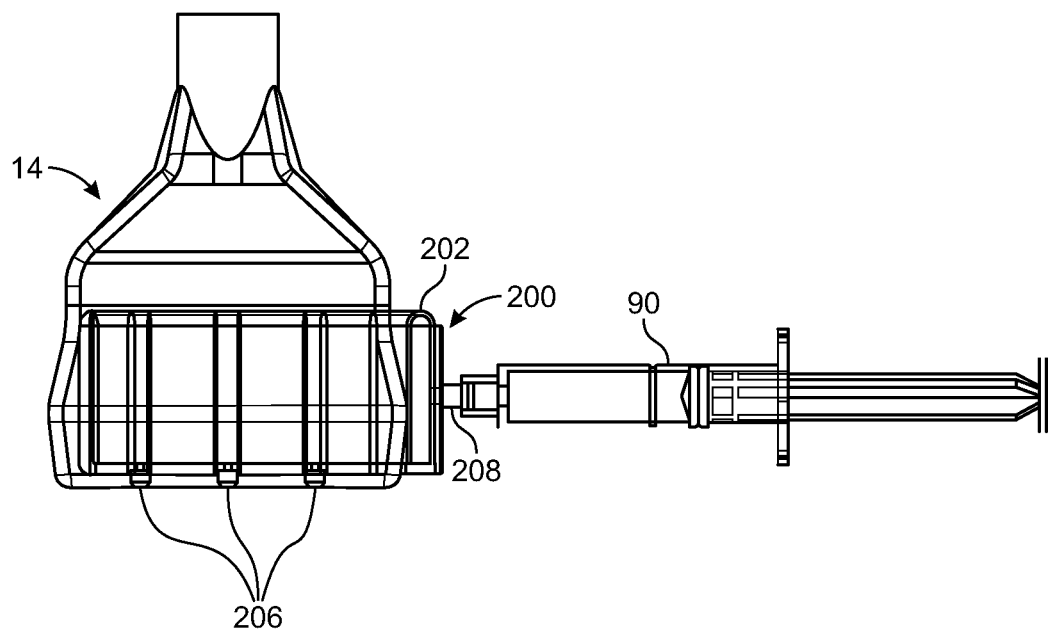
FIG. 26 provides a side view illustration of an embodiment of the accelerator device positioned on the probe along with a replenishing syringe according to an example of the instant disclosure.

FIG. 26 provides a side view illustration of this embodiment of the device 200 positioned on the probe 14. As shown, the accelerator device 200 is slipped over and around the distal end of a probe 14 so that each arm 204a, 204b straddles the probe 14. The arms 204a, 204b are flexible to flex outwardly to allow the probe 14 to be inserted therebetween and provide recoil strength to hold the arms 204a, 204b against the inserted probe 14. In this embodiment, the reservoir 202 is fillable by an inlet port 208 disposed along the reservoir between the arms 204a, 204b. In this embodiment, a syringe 90 is attachable to the inlet port 208 so that additional couplant 37 may be injected into the reservoir 202. Thus, in this embodiment, the inlet port 208 includes a luer fitting that is couplable with conventional syringes.

Figure 27A:
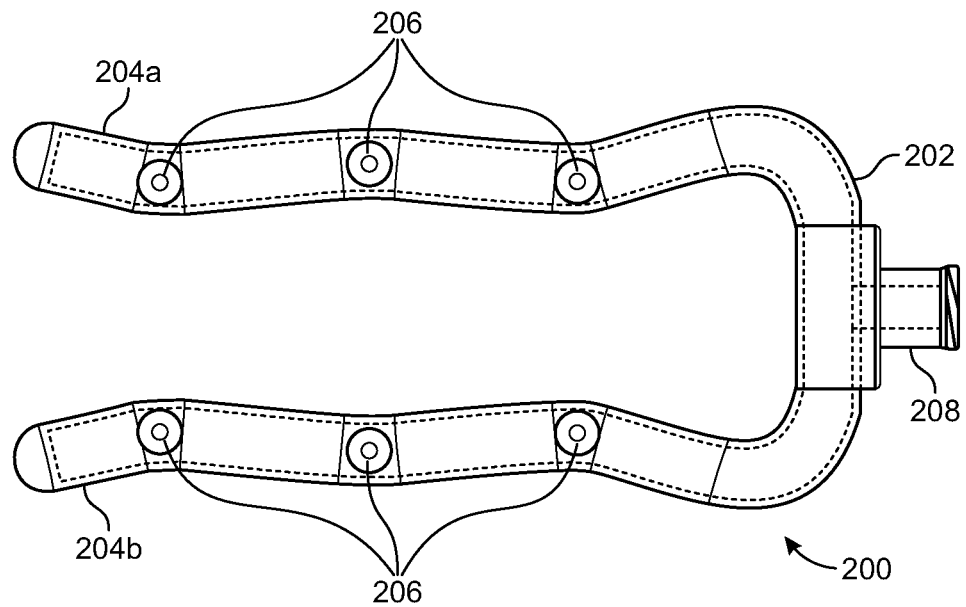
FIGS. 27A-27B provide further illustrations of an embodiment of an accelerator device according to an example of the instant disclosure.
Figure 27B:
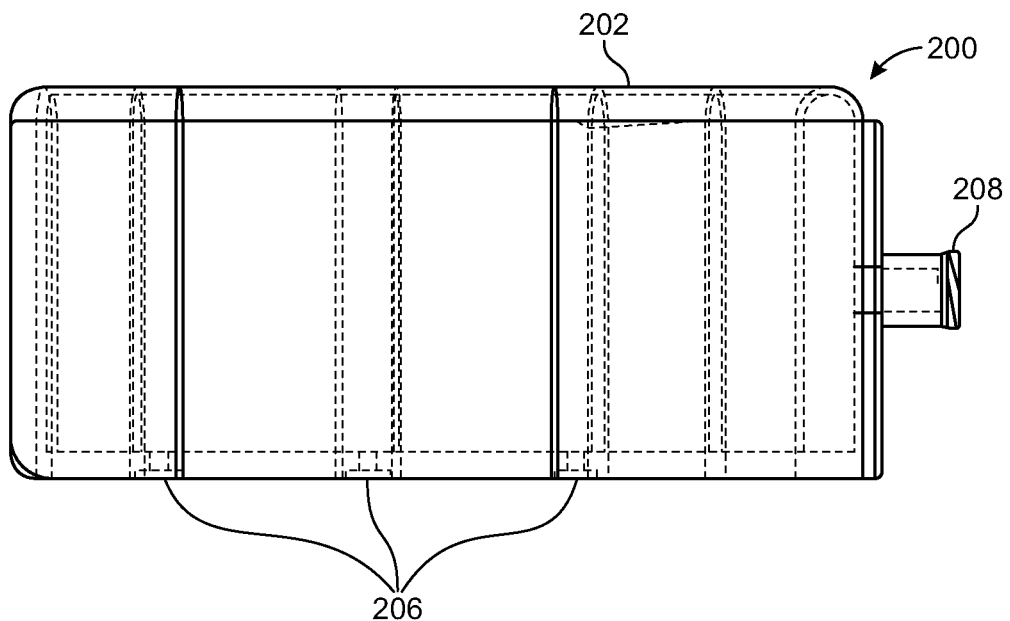

FIGS. 27A-27B provide further illustrations of this embodiment of the accelerator device 200. FIG. 27A provides a view of a bottom surface of the accelerator device 200. Thus, the ports 206 are revealed. In this embodiment, six ports 206 are provided, spaced apart along the bottom surface, three ports 206 along the first arm 204a and three ports along the second arm 204b. It may be appreciated that any number of ports 206 may be present, including one, two, three, four, five, six, seven, eight, nine, ten, or more than ten. Likewise, the ports 206 may be valved or valve-less. Typically the valve is a control valve causing controlled dispensing of the couplant 37. Ports without valves may have controlled flow output due to having a very small opening or multiple small openings. FIG. 27B provides a side view of this embodiment of an accelerator device 200. Again, the ports 206 are shown along the bottom surface of the accelerator device 200.

It may be appreciated that the accelerator device 200 may have a variety of forms. In some embodiments, the accelerator device 200 forms a continuous band having an opening in the center through which the head of the probe 14 is passed. Thus, the accelerator device 200 forms a "ring" around the distal end of the probe 14. Likewise, the accelerator device 200 may only wrap partially around the probe 14. Further, the accelerator device 200 may be attachable to the probe 14 by friction fit or by various attachment mechanisms, such as adhesives, hooks, clamps, tapes, etc. In some embodiments, the accelerator device 200 includes a single reservoir 202. However, in other embodiments, multiple reservoirs 202 may be present including two, three, four, five, six, seven, eight, nine, ten, or more. In some embodiments, the reservoirs 202 are connected by channels so that the reservoirs 202 may be filled by a single inlet port 208 connected to the network of channels. In other embodiments, one or more reservoirs 202 are individually fillable by separate inlet ports. In some embodiments, the one or more reservoirs 202 hold approximately 5 mL of couplant. It may be appreciated that the one or more reservoirs 202 may hold 1 mL, 2 mL, 3 mL, 4 mL, 5 mL, 6 mL, 7 mL, 8 mL, 9 mL, or 10 mL of couplant, or more. It may be appreciated that the accelerator device 200 may be comprised of a variety of materials. In some embodiments, the accelerator device 200 is comprised of plastic, polyethylene, thin walled acrylonitrile butadiene styrene (ABS), silicone or a combination of these. It may be appreciated that in other embodiments the accelerator device 200 is at least partially comprised of metal.

It may be appreciated that the accelerator device 200 may be used with the probe 14 alone (without an ultrashield 10) or in combination with an ultrashield 10. When used without an ultrashield, the accelerator device 200 is attached to the probe 14 so as to dispense couplant 37 as the probe 14 glides over the surface, such as over the skin of the patient. This avoids any need to obtain a separate source of couplant 37 and apply it to the surface. In addition, separate sources of couplant 37, such as tubes of ultrasound gel, are typically non-sterile and are used on patient after patient. By supplying the couplant 37 in the accelerator device 200, the couplant 37 can be sterilized and used with a single patient, reducing or eliminating any cross-contamination between patients. In addition, the couplant 37 is more readily available to the user and deposits the couplant 37 directly in the path of the ultrasound probe 14, increasing image quality and consistency.

As mentioned, the accelerator device 200 may be used in combination with an ultrashield 10. In some embodiments, the ultrashield 10 is positionable on the face of the probe 14 so as to cover the faceplate 12. In some instances portions of the ultrashield 10 wrap around the body of the probe 14, such as the adhesive tabs. In such instances, the accelerator device 200 may be positioned over the portions of the ultrashield 10 wrapped around the probe 14. This still maintains transmission of ultrasound through the faceplate 12 to the area for imaging. In some instances, the ultrashield 10 is attached to or integral with a probe cover 20 which extends along the body of the probe 14. In such instances, the accelerator device 200 may be positioned over the probe cover 20 as this still maintains transmission of ultrasound through the faceplate 12 to the area for imaging. Use of the accelerator device 200 in combination with an ultrashield 10 provides the same advantages as stated above in relation to using the accelerator device 200 alone. In addition, when using the accelerator device 200 with an ultrashield 10, the accelerator device 200 replenishes the couplant layer 32 and/or accelerator membrane 100 as desired, such as during use. This assists in providing sufficient or abundant couplant from the start of imaging (static imaging), through a typical procedure (dynamic imaging), and through longer duration procedures (prolonged imaging), to ensure desired image quality.

It may be appreciated that at least some of the systems, devices and methods described herein may be utilized with other types of equipment other than ultrasound probes. For example, in some instances electrocardiogram (EKG) signals are transmitted through EKG probes. Thus, at least some of the systems, devices and methods described herein may be utilized in conjunction with EKG probes. It may be appreciated that in some embodiments, the body is a human body and in other instances the body is the body of an animal or object.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. An accelerator device for providing couplant while moving an ultrasound probe over a surface comprising:
a reservoir configured to hold ultrasound couplant having at least one arm having an end that flares outwardly and bends inward to make contact with the ultrasound probe in at least one location on the ultrasound probe and forming an open mouth shape that surrounds and straddles opposite sides of the ultrasound probe and wraps at least partially around the ultrasound probe, the at least one arm configured to flex outwardly to allow the ultrasound probe to be inserted therebetween while allowing a head of the probe to make direct contact with a person and comprising a compressible material that reduces in thickness in response to pressure and dispenses the ultrasound couplant, wherein the reservoir is configured to attach to the ultrasound probe so as to dispense the couplant at one or more locations including one or more ports of the at least one arm that are parallel to a faceplate of the ultrasound probe and through openings in response to an amount of pressure applied to the at least one arm, the couplant expelled being correlated to the amount of pressure applied to the at least one arm along a perimeter of the ultrasound probe while moving the ultrasound probe over the surface.

2. The accelerator device of claim 1, wherein the device comprises at least one port along a bottom surface.

3. The accelerator device of claim 2, wherein each of the at least one port comprises a one-way valve.

4. The accelerator device of claim 1, wherein the couplant is delivered at a flow rate of 0.5 to 3 ml per hour.

5. The accelerator device of claim 1, wherein the reservoir comprises two arms connected on one side to create a continuous reservoir within.

6. The accelerator device of claim 5, wherein the two arms are flexible and flex outwardly to allow the probe to be inserted therebetween.

7. The accelerator device of claim 5, the reservoir having an inlet port disposed along the reservoir between the two arms.

8. The accelerator device of claim 1, further comprising an attachment mechanism that attaches to the probe by friction fit, the attachment mechanism comprising one of at least one adhesive, at least one hook, at least one clamp, and at least one tape.

9. The accelerator device of claim 1, wherein the reservoir comprises at least one of plastic, polyethylene, thin walled acrylonitrile butadiene styrene (ABS), and silicone.

* * * * *